US010695277B2

(12) United States Patent
Coulston et al.

(10) Patent No.: US 10,695,277 B2
(45) **Date of Patent: *Jun. 30, 2020**

(54) PRO-FRAGRANCE COMPOSITION

(71) Applicant: AQDOT LIMITED, Cambridge, Cambridgeshire (GB)

(72) Inventors: Roger Coulston, Cambridge (GB); Alexander Tanner, Cambridge (GB); Jose Martinez-Santiago, Cambridge (GB)

(73) Assignee: AQDOT LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/077,852

(22) PCT Filed: Feb. 15, 2017

(86) PCT No.: PCT/GB2017/050395

§ 371 (c)(1),
(2) Date: Aug. 14, 2018

(87) PCT Pub. No.: WO2017/141030

PCT Pub. Date: Aug. 24, 2017

(65) Prior Publication Data

US 2019/0046426 A1 Feb. 14, 2019

(30) Foreign Application Priority Data

Feb. 15, 2016 (GB) .................................. 1602664.3

(51) Int. Cl.

| | |
|---|---|
| ***C11D 3/50*** | (2006.01) |
| ***A61K 8/49*** | (2006.01) |
| ***A61L 9/014*** | (2006.01) |
| ***A61L 9/012*** | (2006.01) |
| ***A61Q 15/00*** | (2006.01) |
| ***A61K 8/33*** | (2006.01) |
| ***A61L 9/01*** | (2006.01) |
| ***A61Q 13/00*** | (2006.01) |

(52) U.S. Cl.

CPC .............. *A61K 8/4946* (2013.01); *A61K 8/33* (2013.01); *A61L 9/01* (2013.01); *A61L 9/012* (2013.01); *A61L 9/014* (2013.01); *A61Q 13/00* (2013.01); *A61Q 15/00* (2013.01); *C11D 3/505* (2013.01); *A61K 2800/57* (2013.01)

(58) Field of Classification Search

CPC ... A61L 9/014; A61L 9/04; A61L 9/01; C11D 3/505

See application file for complete search history.

(56) References Cited

U.S. PATENT DOCUMENTS

| | | | |
|---|---|---|---|
| 5,942,217 | A | 8/1999 | Woo et al. |
| 6,869,466 | B2 | 3/2005 | Day et al. |
| 7,208,464 | B2 | 4/2007 | Heltovics et al. |
| 7,919,452 | B2 | 4/2011 | Malton et al. |
| 2002/0133003 | A1 | 9/2002 | Kim et al. |
| 2003/0068295 | A1 | 4/2003 | Rohde et al. |
| 2003/0140787 | A1 | 7/2003 | Day et al. |
| 2009/0234039 | A1 | 9/2009 | Schutte et al. |
| 2015/0314027 | A1 | 11/2015 | Kim et al. |

FOREIGN PATENT DOCUMENTS

| | | | |
|---|---|---|---|
| GB | 2547281 | A | 8/2017 |
| KR | 10-2006-0088926 | A | 8/2006 |
| KR | 10-2015-0060011 | A | 6/2015 |
| WO | 2014/077640 | A1 | 5/2014 |
| WO | 2014/077641 | A1 | 5/2014 |
| WO | 2014/077642 | A1 | 5/2014 |
| WO | 2014/114345 | A1 | 7/2014 |

OTHER PUBLICATIONS

Apr. 21, 2017 International Search Report issued in International Patent Application No. PCT/GB2017/050394.
Apr. 21, 2017 Written Opinion issued in International Patent Application No. PCT/GB2017/050394.
Lagona, Jason, et al. "The Cucurbit[n]uril Family". Angewandte Chemie International Edition, vol. 44, iss. 31, pp. 4844-4870, 2005.
Del Valle, E.M. Martin, "Cyclodextrins and their uses: a review". Process Biochemistry, 2003, doi:10.1016/S0032-9592(03)00258-9.
Liu, Chuanjun, et al. "Visualization of controlled fragrance release from cyclodextrin inclusion complexes by fluorescence imaging". Flavour and Fragrance Journal, vol. 29, pp. 356-363, 2014.
Kim, Kimoon, et al. "Functionalized cucurbiturils and their applications". Chemical Society Reviews, vol. 36, pp. 267-279, 2007.
U.S. Appl. No. 16/076,848, filed Aug. 9, 2018 in the name of Roger Coulston et al.
Apr. 7, 2017 International Search Report issued in International Patent Application No. PCT/GB2017/050395.
Apr. 7, 2017 Written Opinion issued in International Patent Application No. PCT/GB2017/050395.
Apr. 13, 2020 U.S. Office Action issued U.S. Appl. No. 16/076,848.

*Primary Examiner* — John R Hardee
(74) *Attorney, Agent, or Firm* — Oliff PLC

(57) ABSTRACT

A pro-fragrance composition includes a cucurbituril in complex with a fragrance molecule and use of the compositions in counteracting malodour. The cucurbituril is present as a mixture, wherein the mixture includes at least two different cucurbiturils selected from CB[5], CB[6], CB[7] and CB[8]. The complexed fragrance molecule is released when the composition is exposed to a stimulus. Also provides methods for the preparation of pro-fragrance complexes of cucurbiturils and fragrance molecules.

18 Claims, No Drawings

PRO-FRAGRANCE COMPOSITION

FIELD OF THE INVENTION

This invention relates to compositions comprising physically bound cucurbituril-based pro-fragrances. More particularly, the invention relates to malodour counteracting compositions comprising a mixture of cucurbituril-based pro-fragrance complexes, and to a method to provide such mixtures by mixing at least one fragrance with cucurbiturils having a distribution of sizes, and, optionally, fragrance-free cucurbiturils. The invention relates also to the application of such compositions in perfumery and malodour counteracting.

BACKGROUND

Host-guest complexes have been used in the field of perfumery and for malodour counteracting for some time. For example, U.S. Pat. No. 5,942,217 describes the use of an aqueous solution of cyclodextrin, more generally referred to as cyclic oligosaccharides, for neutralizing malodour. Absorption of the malodour molecule in the cyclodextrin cavity results in efficient mitigation of malodour. The malodour binding process occurs during drying, and low molecular weight polyols can be added to the composition to enhance the formation of cyclodextrin inclusion complexes, especially in the case where the malodour molecule is too small to form a stable inclusion complex. Fragrance molecules may be added to the aqueous solution, and less than about 10% of the cyclodextrin complexes with these molecules.

U.S. Pat. No. 7,208,464 describes cosmetic compositions, comprising between 2 and 20% water, more than 50% of a volatile solvent, such as ethanol, a fragrance oil and a material, such as cyclic oligosaccharides, which is able to provide prolonged, and noticeable, "top note" characteristics. It is believed that when a composition is applied to a substrate an association exists between the perfume raw materials and the entrapment material such that the evaporation of the perfume raw materials is delayed. Over time, this association breaks down resulting in release of the perfume raw materials. The result is that the "top note" character continues to be experienced by the user over time.

However, in U.S. Pat. No. 7,919,452 C1-C8 alkyl-substituted cyclic oligosaccharides having an average degree of substitution from 1.6 to about 2.8 are described as delaying the release of volatile solvents and also reducing the initial harsh alcoholic odour impact of an alcoholic or hydro-alcoholic cosmetic composition. It is described that the volatile solvent itself competes with the perfume oils for docking in the cyclic oligosaccharide cavity. This results in some "in situ complex formation" between the volatile solvent and the cyclic oligosaccharide. It is believed that the stability profile of this cyclic oligosaccharide—volatile solvent complex is such that there is a delay in the release of the volatile solvent from the composition when applied to a substrate. It is further believed that this results in a perceptible reduction in initial solvent release thus satisfying the consumer desire for a reduced initial harsh solvent odour upon application of the composition.

As is apparent from the above prior art, the action of cyclodextrin on the perception of both malodours and perfumes depends strongly on the activity of water in the system. This reflects complex equilibria involving water, fragrance and malodour inclusion in the cyclodextrin cavity. Hence, the apparent host-guest binding constant may vary for both fragrances and malodours, depending on the concentration of water in the system. The poor predictability of such, essentially non-equilibrium effects, is a source of recurring difficulties for the perfumer. The poor selectivity of cyclodextrin binding and release with respect to fragrances and malodours is a disadvantage. Although this effect can be beneficial in the context of the controlled release of a desirable odour, it becomes very unsatisfactory if the guest molecule released is a malodour.

Another disadvantage of cyclodextrins is the tendency of these carbohydrate-derived materials to become sticky at low water levels or with decreasing water activity. This can lead to, for example, an undesirable "tacky" feeling on the skin. Finally, as is usually the case with aqueous carbohydrate solutions, aqueous cyclodextrin solutions must be preserved against micro-organism invasion using significant amounts of preservatives.

In view of the disadvantages associated with cyclodextrin, alternative host-guest systems are desirable which overcome these problems. In U.S. Pat. No. 6,869,466, a method is described to bind a gas or a volatile molecule to a cucurbituril to form an inclusion complex as well as steps for releasing at least some of the bound gas or volatile compounds. Trapping malodorous compounds is mentioned as an example of application. The formation of the host-guest complex is described as occurring in both dry state, for example with the cucurbituril host molecules adsorbed or supported on a solid surface or dissolved or dispersed in a liquid, for example water.

WO2014077641 describes a composition comprising a complex of cucurbit[7]uril and a fragrance molecule for use in odour removal and provides some evidence that a fragrance molecule is released when an odour molecule is bonded to the cucurbit[7]uril host molecule.

In a pro-fragrance, the fragrance is generally bound covalently to an odourless substrate or another fragrance. The pro-fragrance may be synthesized by a chemist or may occur spontaneously in a mixture. Known examples of spontaneous pro-fragrances are Schiff bases that occur following the reversible reaction between anthranilates and aldehydes. When applied to a surface, such Schiff bases have a low to moderate odour, while after a certain time and under the action of moisture and temperature, both powerful anthranilate and aldehyde are released, providing a prolonged perception of both molecules on the surface. Pro-fragrances therefore have a variety of applications in fragrance related products.

Although cucurbituril host-guest complexes overcome many of the disadvantages associated with cyclodextrin complexes, there is a need for a pro-fragrance composition where the fragrance performance attributes, including perfume accord and release profile, can be selected and optimised according to objective criteria.

SUMMARY OF THE INVENTION

The present invention generally provides a pro-fragrance composition comprising fragrance molecules and a mixture of at least two different cucurbiturils selected from CB[5], CB[6], CB[7] and CB[8] cucurbiturils, wherein the fragrance molecules are complexed with the cucurbiturils. The fragrance molecules are released from the complexes upon exposure of the complexes to a trigger. The fragrance molecules may be the same or may be a mixture of different fragrance molecules.

The inventors have found that fragrance-cucurbituril complexes can be considered and used as a new class of pro-fragrances. A pro-fragrance composition comprising a distribution of cucurbiturils provides optimal malodour counteracting performance and the mixture of cucurbiturils can be adjusted depending on fragrance performance attributes required by the perfumer. In addition to moisture- or water-induced release, a change of ionic strength or pH of the composition provides an advantage over prior art fragrance-cucurbituril complexes which rely on the presence of malodour molecules to displace and release the fragrance.

In one aspect, there is provided a pro-fragrance composition comprising a plurality of complexes of cucurbituril with one or more fragrance molecule(s), wherein the cucurbiturils are present as a mixture comprising two or more different cucurbiturils selected from CB[5], CB[6], CB[7] and CB[8], whereby the fragrance is released when the complexes are exposed to a trigger.

In one embodiment, the composition comprises CB[6] and CB[7]. In another embodiment, the composition comprises CB[6], CB[7] and CB[8].

In another embodiment, the composition comprises substantially fragrance-free CB[5] cucurbituril.

In one embodiment, the composition comprises less than 5% by weight, more particularly less than 1% by weight, more particularly less than 0.5% by weight of CB[5] complexed with fragrance, based on the total weight of CB[5] in the composition.

In one embodiment, the complex has a binding constant of at least 10 $M^{-1}$, in particular at least 100 $M^{-1}$, more particularly the binding constant is at least 1000 $M^{-1}$.

In another embodiment, the stimulus or trigger required to release the fragrance from the fragrance-cucurbituril complex is an increase of moisture, an addition of liquid water to the composition, a change in the ionic strength or pH of the composition. Alternatively, the stimulus may be the application of heat to the composition. Molecular displacement may instead be used to trigger release of the fragrance.

The cucurbituril is present in the composition as a mixture of at least two different sized cucurbiturils selected from CB[5], CB[6], CB[7] and CB[8]. Where the cucurbituril is referred to as cucurbit[n]uril, the composition comprises a mixture of different sized cucurbit[n]urils, wherein n is an integer from 4 to 20 and wherein the mixture comprises at least two different cucurbiturils selected from the group consisting of CB[5], CB[6], CB[7] and CB[8].

In a further aspect there is provided a consumer product comprising a pro-fragrance composition having a plurality of complexes of cucurbiturils with fragrance molecules, wherein the cucurbiturils are present as a mixture, wherein the mixture comprises at least two different cucurbiturils selected from CB[5], CB[6], CB[7] and CB[8], whereby the fragrance molecules are released when the composition is exposed to a stimulus.

In another aspect there is provided a method for the preparation of fragrance-cucurbituril complexes wherein the cucurbiturils are present as a mixture, wherein the mixture comprises at least two different cucurbiturils selected from CB[5], CB[6], CB[7] and CB[8], the method comprising the step of mixing a fragrance solution with the cucurbiturils, thereby to form complexes of the cucurbiturils with the fragrance.

These and other aspects and embodiments of the invention are described in further detail below.

DETAILED DESCRIPTION OF THE INVENTION

The present inventors have found that a mixture of cucurbiturils may be used to physically bind to a fragrance molecule to form a mixture of different sized cucurbituril complexes, providing a pro-fragrance composition. The inventors have found that a pro-fragrance composition comprising a mixture of different sized cucurbituril provides enhanced fragrance and malodour counteracting properties.

Furthermore, when a mixture of fragrances is used, for example in the form of a perfumery accord, a pro-fragrance composition comprising a mixture of different sized cucurbiturils provides a better preservation of the odour characteristics of the perfumery accord, such as odour direction and hedonic aspect and pleasantness, compared to systems where a single cucurbituril size is used, or a cyclodextrin is used.

In a composition comprising only single-sized cucurbituril or cyclodextrin, the odour characteristics of the perfumery accord are usually deformed and the original odour not always similar to that of the original perfumery accord. The release profile of the accord as function of time may also be affected with some notes being released before others. These undesirable effects are suppressed when using a mixture of different sized cucurbiturils, according to the present invention.

The fragrance may be released from the complex when exposed to a stimulus. The stimulus is not limited to molecular exchange but may be a change in humidity, ionic strength or pH of the composition. The pro-fragrance compositions of the invention are therefore useful in applications requiring controlled fragrance release, as well as in applications requiring the masking of malodour.

The pro-fragrance composition may further comprise fragrance-free cucurbituril. The present inventors have found that the presence of fragrance-free cucurbituril, in particular CB[5], in the pro-fragrance composition results in enhanced malodour counteracting properties as the CB[5] can form a complex with small malodour molecules, masking their unpleasant smell.

Cucurbituril

The present invention provides the use of a cucurbituril to form a complex with a fragrance molecule.

Cucurbituril is a member of the cavitand family, and the general cucurbituril structure is based on the cyclic arrangement of glycoluril subunits linked by methylene bridges.

The preparation and purification of cucurbituril compounds is well described in the art. For example, Lagona et al. review the synthesis and properties of cucurbituril compounds, including derivatives, analogues and congener within the cucurbituril family.

For example, cucurbit[8]uril (CB[8]; CAS 259886-51-6) is a barrel shaped container molecule which has eight repeat glycoluril units and an internal cavity volume of 479 $A^3$ (see structure below). CB[8] is readily synthesised using standard techniques and is available commercially (e.g. Sigma-Aldrich, MO USA).

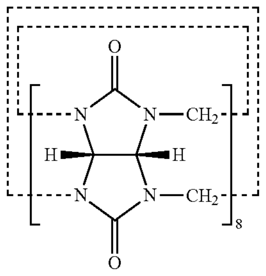

The cucurbituril in the pro-fragrance composition is present as a mixture of two or more CB[n], wherein the mixture comprises at least two different cucurbituril selected from CB[5], CB[6], CB[7] and CB[8] and where n is an integer from 4 to 20.

Other cucurbituril may be present in the composition in addition to CB[5], CB[6], CB[7] and CB[8]. For example, the composition may further comprise cucurbiturils of CB[n] where n is an integer of 4 or 9 to 20 (e.g. CB[9], CB[10], CB[11] etc.). For example the composition may further comprise, CB[4] or CB[9], or CB[4] and CB[9].

When CB[5] is present in the cucurbituril mixture, the concentration of CB[5] may be from about 0.1 to about 99% by weight, more particularly from about 0.5 to about 75% by weight, more particularly from about 1 to about 50% by weight, more particularly from about 2 to about 30% by weight, more particularly from about 5 to about 25% by weight, more particularly from about 10 to about 20% by weight, based on the total weight of the cucurbituril in the composition.

In one embodiment, the composition may comprise substantially fragrance-free CB[5]. The term “substantially fragrance-free” means that less than 5% by weight, more particularly less than 1% by weight, more particularly less than 0.5% by weight of the CB[5] in the composition is complexed with fragrance, based on the total weight of CB[5] in the composition.

When CB[6] is present in the cucurbituril mixture, the concentration of CB[6] may be from about 0.1 to about 99% by weight, more particularly from about 1 to about 75% by weight, more particularly from about 5 to about 60% by weight, more particularly from about 20 to about 55% by weight, more particularly from about 35% by weight to about 55% by weight, based on the total weight of cucurbituril in the composition.

When CB[7] is present in the cucurbituril mixture, the concentration of CB[7] may be from about 0.1 to 99% by weight, more particularly from about 5 to about 75% by weight, more particularly from about 10 to about 60% by weight, more particularly from about 20% by weight to about 45% by weight, based on the total weight of cucurbituril in the composition. In one embodiment, the concentration of CB[7] is less than 45% by weight, based on the total weight of cucurbituril in the composition.

When CB[8] is present in the cucurbituril mixture, the concentration of CB[8] may be from about 0.1 to 99% by weight, more particularly from about 0.5 to about 75% by weight, more particularly from about 1 to about 30% by weight, more particularly about 5 to about 25% by weight, more particularly from about 10 to about 20% by weight, based on the total weight of cucurbituril in the composition.

The total concentration of the at least two different cucurbiturils selected from CB[5], CB[6], CB[7] and CB[8] may be greater than 75% by weight, more particularly greater than about 90% by weight, more particularly greater than about 99% by weight of the total weight of cucurbituril in the composition. The remaining components of the cucurbituril mixture may contain CB[4], CB[9] and/or higher cucurbiturils (i.e. CB[10]-CB[20]), either as a single sized cucurbituril or as a mixture of these sizes.

In a particular embodiment, the cucurbituril mixture comprises between 12 and 17% by weight of CB[5]; 45 and 50% by weight of CB[6]; 22 and 27% by weight of CB[7]; 12 and 17% by weight of CB[8]; and less than 1% by weight of CB[9] and higher cucurbiturils, based on the total weight of cucurbituril in the composition.

The % weights of cucurbituril described above are based on the total weight of cucurbituril (of all sizes) in the composition. The cucurbituril mixture used as the starting material to prepare the compositions of the invention, i.e. the mixture of uncomplexed cucurbituril, will have the same weight percentages as described above.

In some embodiments, all of the cucurbituril in the composition will be complexed. The composition may comprise complexed cucurbituril and uncomplexed cucurbituril. The uncomplexed cucurbituril may be CB[5].

In other aspects of the invention, cucurbituril derivatives are provided and find use in the methods described herein. A derivative of a cucurbituril is a structure having one, two, three, four or more substituted glycoluril units. A substituted cucurbituril compound may be represented by the structure below:

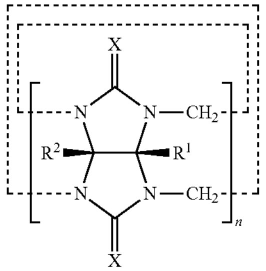

wherein:

n is an integer between 4 and 20;

and for each glycoluril unit:

each X is O, S or $NR^3$, and

—$R^1$ and —$R^2$ are each independently selected from —H and the following optionally substituted groups: —$R^3$, —OH, —$OR^3$, —COOH, —$COOR^3$, —$NH_2$, —$NHR^3$ and —$N(R^3)_2$ where —$R^3$ is independently selected from $C_{1-20}$alkyl, $C_{6-20}$carboaryl, and $C_{6-20}$heteroaryl, or where —$R^1$ and/or —$R^2$ is —$N(R^3)_2$, both —$R^3$ together form a $C_{5-7}$ heterocyclic ring; or together —$R^1$ and —$R^2$ are $C_{4-6}$alkylene forming a $C_{6-8}$carbocyclic ring together with the uracil frame.

In one embodiment, one of the glycoluril units is a substituted glycoluril unit. Thus, —$R^1$ and —$R^2$ are each independently —H for n−1 of the glycoluril units In one embodiment, n is 5, 6, 7, 8, 9, 10, 11 or 12.

In one embodiment, n is 5, 6, 7 or 8.

In one embodiment, each X is O.

In one embodiment, each X is S.

In one embodiment, $R^1$ and $R^2$ are each independently H.

In one embodiment, for each unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In this embodiment, the remaining glycoluril units are such that $R^1$ and $R^2$ are each independently H.

Preferably —$R^3$ is $C_{1-20}$alkyl, most preferably $C_{1-6}$alkyl. The $C_{1-20}$alkyl group may be linear and/or saturated. Each group —$R^3$ may be independently unsubstituted or substituted. Preferred substituents are selected from: —$R^4$, —OH, —SH, —$SR^4$, —COOH, —$COOR^4$, —$NH_2$, —$NHR^4$ and —$N(R^4)_2$, wherein —$R^4$ is selected from $C_{1-20}$alkyl, $C_{6-20}$carboaryl, and $C_{5-20}$heteroaryl. The substituents may be independently selected from —COOH and —$COOR^4$.

In some embodiments, —$R^4$ is not the same as —$R^3$. In some embodiments, —$R^4$ is preferably unsubstituted.

When —$R^1$ and/or —$R^2$ is —$OR^3$, —$NHR^3$ or —$N(R^3)_2$, then —$R^3$ is preferably $C_{1-6}$alkyl. In some embodiments, —$R^3$ is substituted with a substituent —$NHR^4$ or —$N(R^4)_2$. Each —$R^4$ is $C_{1-6}$alkyl and is itself preferably substituted.

In one embodiment, references to a cucurbituril compound are references to derivatives thereof. The cucurbiturils of the invention may be in the native form or they may be modified as described above in order to improve their solubility, dispersibility, and more generally their formulation and handling.

Complex

In one aspect the present invention provides a pro-fragrance complex of a cucurbituril with a fragrance molecule.

As used herein, the term "pro-fragrance" means a substantially odourless or low odour material that releases one or more fragrance(s) under the action of a trigger or stimulus, such as an increase in moisture, an increase of temperature, a change of pH or a chemical reaction, such as a hydrolysis or an oxidation.

As used herein, the term "fragrance" refers to both a r fragrance molecule, as well as a mixture of fragrance molecules that are used to impart an overall pleasant odour profile to a composition, particularly a cosmetic composition. A wide variety of chemicals are useful as, fragrance molecules including materials such as aldehydes, ketones and esters, which may be synthetic or may be derived from naturally occurring plant or animal sources. Suitable fragrance molecules are included below.

The pro-fragrance complexes described herein are formed from cucurbituril, which acts as the host, and a fragrance molecule which acts as the guest. The fragrance is physically bound to the cucurbituril substrate instead of being covalently bound to the substrate as is the case for classical pro-fragrances. The terms "physically bound", "physical bonding" and "physical linkage" used throughout include bonding by Van der Waals forces and other types of physical bond. In the present context, hydrogen bonds are also considered as physical bonds. Physical bonding has considerable advantages over chemical bonding, such as mild conditions of formation of the pro-fragrance, absence of side reactions leading to potentially undesired products, and the fact that the entity formed is not a new molecule means that registration rules do not apply.

Another advantage of physical binding in the pro-fragrance context is the possibility to use non- or less reactive fragrances, such as hydrocarbons, esters, oxides and ethers, for which classical pro-fragrances are scarce or inexistent.

Furthermore, physical binding allows the formation of pro-fragrances with a multitude of fragrances having a multitude of chemical structures and functions.

The cucurbituril-fragrance complex may be a ternary or a binary complex. Thus, the cucurbituril may hold one or two guest fragrance molecules within its cavity. Where a cucurbituril holds two fragrance molecules, the fragrance molecules may be the same or they may be different. A cucurbituril that is capable of hosting two fragrance molecules may also be capable of forming a stable binary complex with a single fragrance. The formation of a ternary guest-host complex is believed to proceed via an intermediate binary complex.

In one embodiment, the cucurbituril is capable of forming a ternary complex. For example, CB[8] is capable of forming a ternary complex.

In one embodiment, the cucurbituril is capable of forming a binary complex. CB[8] may also form a binary complex.

In one embodiment, the cucurbituril is capable of forming ternary and binary complexes. For example, CB[8] is capable of forming a ternary or a binary complex, depending upon the nature of the guest.

The formation of the complex is reversible. The decomplexation of the complex to separate the cucurbituril from the guest fragrance or fragrances may be achieved by, for example, heating the complex, exposing the complex to moisture or liquid water, evaporation, or by introducing a competitive agent, i.e. by molecular exchange. This is discussed in further detail below in relation to fragrance release.

The applicant has established that to perform as a pro-fragrance, a fragrance-cucurbituril complex must have a binding constant preferably larger than 10 $M^{-1}$. In one embodiment, the binding constant is at least 10 $M^{-1}$ or at least 100 $M^{-1}$. In one embodiment, the binding constant is at least 10 $M^{-1}$ or at least 100 $M^{-1}$ or at least 1000 $M^{-1}$.

The binding constant for a binary complex between a fragrance molecule F and a cucurbituril CB[x], where x is an integer selected from 4 to 20, is defined according to the Le Chatelier principle of mass action as:

$$F+CB[x] \leftrightarrows FCB[x]$$

$$K=[FCB[x]]/([F]*[CB[x]])]$$

where the square brackets denote the concentration of the species in mol/l.

In one embodiment, the pro-fragrance composition comprises pro-fragrance complexes with a distribution of binding constants. In order to perform in a broad range of applications, the applicant has found that pro-fragrances characterised by a distribution of binding constants are more advantageous than pro-fragrances characterised by a single binding constant. For example, pro-fragrances characterised by a distribution of binding constants may release the fragrance linearly over time, with the less tightly bound fragrance released first (e.g. during the first hours after application of the pro-fragrance), and the more tightly bound fragrance released later (e.g. during several days after application of the pro-fragrance), or upon the application of a trigger, such as heat.

Fragrance

The selection of fragrances suitable for the present invention is broad in terms of chemical structure and odour characteristics. Suitable fragrances include fragrance molecules, such as alcohols, aldehydes, ketones, lactones and O-heterocycles, ethers, acetals, ketals, N- and S-compounds, hydrocarbons and terpenes; and essential oils, wherein essential oil comprise one or more fragrance molecules.

Examples of suitable fragrance molecules include the following:

Alcohols, such as but not limited to (−)-3-Neoisothujanol; (−)-Thujol (21653-20-3); (−)-Sclareol (515-03-7); (+)-Cedrol (77-53-2); (+/−)-2,4,8-Trimethyl-7-nonen-2-ol (437770-28-0); (+/−)-2-Methyl-1-butanol (137-32-6); (+/−)-4-Mercapto-4-methyl-2-pentanol (31539-84-1); (+/−)-trans- and cis-4,8-Dimethyl-3,7-nonadien-2-ol (67845-50-5); (E)-2-Decenol (18049-18-2); (E)-2-Octen-1-ol (18409-17-1); (E)-2-Octen-4-ol (20125-81-9); (E)-3-(Z)-6-Nonadien-1-ol (56805-23-3); (E,E)-2,4-Decadien-1-ol (18409-21-7); (E,E)-2,4-Hexadien-1-ol (111-28-4); (E,R)-3,7-Dimethyl-1,5,7-octatrien-3-ol (20053-88-7); (R)-(−)-1-Octen-3-ol (3687-48-7); (Z)(Z)-3,6-Nonadien-1-ol (53046-97-2); (Z)-2-Hexen-1- ol (928-94-9); (Z)-4-Hepten-1-ol (6191-71-5); 10,11-Dihydrofarnesol (7226-86-0); 1-Decen-3-ol (51100-54-0); 1-Hexen-3-ol (4798-44-1); 1-Octanol (111-87-5); 1-Octen-3-ol (3391-86-4); 1-Penten-3-ol (616-25-1); 1-Phenyl-1-propanol (93-54-9); 2(10)-Pinen-3-ol (5947-36-4); 2,3-Dihydrofarnesol (51411-24-6); 2,6-nonadienol (28069-72-9); 2-Ethyl-1-hexanol (104-76-7); 2-Ethyl-fenchol (18368-91-7); 2-Heptanol (543-49-7); 2-Hexen-1-ol (2305-21-7); 2-Methyl-4-phenyl-2-butanol (103-05-9); 2-Nonanol (628-99-9); 2-Octanol (123-96-6); 2-Phenoxy ethanol (122-99-6); 2-Undecanol (1653-30-1); 2-Undecen-1-ol (37617-03-1); 3,5,5-Trimethyl-1-hexanol (3452-97-9); 3,7-Dimethyl-1-octanol (106-21-8); 3-Decanol (1565-81-7); 3-Heptanol (589-82-2); 3-Octanol (589-98-0); 3-Octen-2-ol (76649-14-4); 3-Phenyl-1-propanol (122-97-4); 4-Hexen-1-ol (6126-50-7); 4-Phenyl-2-butanol (2344-70-9); 4-Phenyl-3-buten-2-ol (17488-65-2); 4-Thujanol; Sabinene hydrate (546-79-2); 5-Phenylpentanol (10521-91-2); 6,7-Dihydrofarnesol (92857-01-7); 6-Hydroxydihydrotheaspirane (65620-50-0); 9-Decenol (13019-22-2); alpha,alpha-Dimethylphenethyl alcohol (100-86-7); alpha-Amylcinnamyl alcohol (101-85-9); alpha-Bisanolol (515-69-5); alpha-Isobutylphenethyl alcohol (7779-78-4); alpha-Ionol (25312-34-9); alpha-Propylphenethyl alcohol (705-73-7); alpha-Santalol (115-71-9); alpha-Terpineol (98-55-5); 1-(2-Tert-butylcyclohexyl)oxybutan-2-ol (139504-68-0); beta-Ionol (22029-76-1); beta-Methylcrotyl alcohol; 2-Methyl-but-2-en-1-ol (4675-87-0); beta-Methylphenethyl alcohol (1123-85-9); ethyl 6-(acetyloxy) hexanoate (104986-28-9); Borneol (507-70-0); Caryophyllene alcohol (4586-22-5); Cinnamyl alcohol (104-54-1); cis,trans-2-Methyl-2-vinyl-5-(2-hydroxy-2-propyl)tetrahydrofuran (5989-33-3); cis-2,8-p-Menthadien-1-ol (22771-44-4); cis-2-Nonen-1-ol (41453-56-9); cis-3-Hexen-1-ol (928-96-1); cis-3-Nonen-1-ol (10340-23-5); cis-3-Octen-1-ol (20125-84-2); cis-4-Decenol (57074-37-0); cis-5-Octen-1-ol (64275-73-6); cis-6-Nonen-1-ol (35854-56-5); cis-9-Octadecenol (143-28-2); Cubebol (23445-02-5); 2-trans, 6-cis-nonadienol (7786-44-9); Decanol (112-30-1); Dihydro linalool (2270-57-7); Di hydro myrcenol (18479-58-8); Dihydro-beta-ionol (3293-47-8); dl-Citronellol (106-22-9); (Z)-3-methyl-5-(2,2,3-trimethyl-1-cyclopent-3-enyl)pent-4-en-2-ol (67801-20-1); Ethyl linalool (10339-55-6); Farnesol (4602-84-0); Fenchyl alcohol (1632-73-1); Geraniol (106-24-1); Heptanol (111-70-6); Hexanol (111-27-3); Hydroxycitronellal diethyl acetal (7779-94-4); Hydroxycitronellal dimethyl acetal (141-92-4); Hydroxycitronellal propyleneglycol acetal (93804-64-9); Isoborneol (124-76-5); Isobutanol (78-83-1); 1-methyl-2-1,2,2-trimethyl-3-bicyclo[3.1.0] hexanyl]methyl]cyclopropyl]methanol (198404-98-7); Lauryl alcohol (112-53-8); Linalool (78-70-6); Linalool oxide pyranoid (14049-11-7); Mayol (5502-75-0); Nerol; (Z)-Geraniol (106-25-2); Nerolidol; FCI-119b (7212-44-4); Nonanol; Nonyl alcohol (143-08-8); Patchouli alcohol (5986-55-0); p-Cymen-8-ol; NSC-361057 (1197-01-9); Phenethylmethylethylcarbinol (10415-87-9); p-Menth-1-en-9-ol (18479-68-0); Phenyl ethyl alcohol (60-12-8); (E)-3,3-Dimethyl-5-(2,2, 3-trimethyl-3-cyclopenten-1-yl)-4-penten-2-ol (107898-54-4); Prenol; Prenyl alcohol (556-82-1); (E)-2-ethyl-4-(2,2,3-trimethyl-1-cyclopent-3-enyl)but-2-en-1-ol (28219-61-6); Rhodinol (6812-78-8); m-(isocamphyl-5)cyclohexanol (66068-84-6); Tetrahydrolinalool (78-69-3); trans- and cis-2,4,8-Trimethyl-3,7-nonadien-2-ol (479547-57-4); trans-2-Nonen-1-ol (31502-14-4); trans-2-trans-4-Heptadien-1-ol (33467-79-7); trans-3-Hexenol (928-97-2); Undecyl alcohol (112-42-5); 4-methyldec-3-en-5-ol (81782-77-6); Verbenol; (+)-Verbenol (473-67-6); and Vetiverol (89-88-3).

Esters, carbonates and glycolates, such as but not limited to (−)-Campholenyl acetate (36789-59-0); (+/−) Ethyl 2-hydroxy-2-methylbutyrate (77-70-3); (+/−) Ethyl 2-hydroxy-3-methylvalerate (24323-38-4); (+/−)-Ethyl 3-acetoxy-2-methylbutrate (139564-43-5); (+/−)-Ethyl 3-hydroxy-2-methylbutyrate (27372-03-8); (+/−)-Heptan-2-yl butyrate (39026-94-3); (+/−)-Heptan-3-yl acetate (5921-83-5); (+/−)-Methyl 5-acetoxyhexanoate (35234-22-1); (+/−)-Nonan-3-yl acetate (60826-15-5); (+/−)-Octan-3-yl formate (84434-65-1); (+/−)-trans- and cis-4,8-Dimethyl-3,7-nonadien-2-yl acetate (91418-25-6); (E)-2-Hexenyl formate (53398-78-0); (E)-2-Hexenyl hexanoate (53398-86-0); (E,Z)-2,6-Nonadien-1-ol acetate (68555-65-7); (E,Z)-3,6-Nonadien-1-ol acetate (211323-05-6); (Z)-3- & (E)-2-Hexenyl propionate (53398-80-4); (Z)-3-Hexenyl (E)-2-butenoate (65405-80-3); (Z)-3-Hexenyl pyruvate (68133-76-6); (Z)-5-Octenyl propionate (196109-18-9); 1,3,3-Trimethyl-2-norbornanyl acetate (13851-11-1); 1,3-Nonanediol acetate (mixed esters) (1322-17-4); 10-Undecen-1-yl acetate (112-19-6); 1-Ethoxyethyl acetate; (1608-72-6); 1-Ethylhexyl tiglate (94133-92-3); 1-Octen-3-yl butyrate (16491-54-6); 1-p-Menthen-9-yl acetate (17916-91-5); 2-(E)Hexen-1-yl acetate (2497-18-9); 2,4-Hexadienyl acetate (1516-17-2); 2,4-Hexadienyl butyrate (16930-93-1); 2,4-Hexadienyl isobutyrate (16491-24-0); 2,4-Hexadienyl propionate (16491-25-1); 2,5-Dimethyl-3-oxo-(2H)-fur-4-yl butyrate (114099-96-6); 2-Ethylbutyl acetate (10031-87-5); 2-Hexenyl octanoate (85554-72-9); 2-Hexyl-4-acetoxytetrahydrofuran (10039-39-1); 2-Hydroxymethyl-6,6-dimethylbicyclo(3.1.1)hept-2-enyl formate (72928-52-0); 2-Methyl-4-phenyl-2-butyl acetate (103-07-1); 2-Methyl-4-phenyl-2-butyl isobutyrate (10031-71-7); 2-Methylallyl butyrate (7149-29-3); 2-Methylbutyl 2-methylbutyrate (2445-78-5); 2-Methylbutyl 3-methyl-2-butenoate (97890-13-6); 2-Methylbutyl 3-methylbutanoate (2445-77-4); 2-Methylbutyl acetate (624-41-9); 2-Pentyl 2-methylpentanoate (90397-36-7); 2-Pentyl acetate (626-38-0); 2-Pentyl butyrate (60415-61-4); 2-Phenoxyethyl isobutyrate (103-60-6); 2-Phenyl-3-carbethoxy furan (50626-02-3); 2-Phenylpropyl butyrate (80866-83-7); 2-Phenylpropyl isobutyrate (65813-53-8); 3-Hexenyl 2-hexenoate (53398-87-1); 3-Hexenyl 2-methylbutanoate (10094-41-4); 3-Hexenyl 3-methylbutanoate (10032-11-8); 3-Hexenyl phenylacetate (42436-07-7); 3-Methylbutyl 2-methylbutanoate (27625-35-0); 3-Methylbutyl 2-methylpropanoate (2050-01-3); 3-Octyl acetate (4864-61-3); 3-Octyl butyrate (20286-45-7); 3-Phenylpropyl acetate (122-72-5); 3-Phenylpropyl cinnamate (122-68-9); 3-Phenylpropyl formate (104-64-3); 3-Phenylpropyl hexanoate (6281-40-9); 3-Phenylpropyl isobutyrate (103-58-2); 3-Phenylpropyl isovalerate (501-52-0); 3-Phenylpropyl propionate (122-74-7); 4-(tert-butyl)cyclohexyl acetate (32210-23-4); 4-Acetoxy-2,5-dimethyl-3(2H)furanone (4166-20-5); 4-Methylpentyl isovalerate (850309-45-4); 4-Pentenyl acetate (1576-85-8); 4-Phenyl-2-butyl acetate (10415-88-0); 6-Acetoxydihydrotheaspirane (57893-27-3);

6-Methyl-5-hepten-2-yl acetate (19162-00-6); 8-Ocimenyl acetate (197098-61-6); Acetoin acetate (4906-24-5); Acetyleugenol (93-28-7); Alicate (10250-45-0); Allyl 10-undecenoate (7493-76-7); Allyl amyl glycolate (67634-00-8); Allyl butyrate (2051-78-7); Allyl cyclohexaneacetate (4728-82-9); Allyl cyclohexanebutyrate (7493-65-4); Allyl cyclohexanepropionate, Ananolide (2705-87-5); Allyl cyclohexanevalerate (7493-68-7); Allyl heptanoate (142-19-8); Allyl hexanoate (123-68-2); Allyl isovalerate (2835-39-4); Allyl phenoxyacetate (7493-74-5); Allyl phenylacetate (1797-74-6); Allyl propionate (2408-20-0); Allyl sorbate (30895-79-5); Allyl tiglate (7493-71-2); Allyl valerate (6321-45-5); alpha,alpha-Dimethylbenzyl isobutyrate (7774-60-9); alpha,alpha-Dimethylphenethyl acetate (151-05-3); alpha-Amylcinnamyl acetate (7493-78-9); alpha-Amylcinnamyl formate (7493-79-0); alpha-Amylcinnamyl isovalerate (7493-80-3); alpha-Ethyl benzyl butyrate (10031-86-4); alpha-Isomethylionyl acetate (68555-61-3); alpha-Methylbenzyl formate (7775-38-4); alpha-Methylbenzyl isobutyrate (7775-39-5); alpha-Santalol phenylacetate (77-88-3); alpha-Santalyl acetate (1323-00-8); alpha-Terpinyl anthranilate (14481-52-8); alpha-Terpinyl formate (2153-26-6); alpha-Terpinyl isobutyrate (7774-65-4); Amyl 2-furoate (1334-82-3); Amyl butyrate (540-18-1); Amyl formate (638-49-3); Amyl heptanoate (7493-82-5); Amyl hexanoate (540-07-8); Amyl octanoate (638-25-5); Amyl salicylate (2050-08-0); Amylvinylcarbinol acetate (2442-10-6); Anisyl acetate (104-21-2); Anisyl butyrate (6963-56-0); Anisyl formate (122-91-8); Anisyl phenylacetate (102-17-0); Anisyl propionate (7549-33-9); Benzoyl eugenol (531-26-0); Benzyl 2,3-dimethylcrotonate (77492-69-5); Benzyl acetate (140-11-4); Benzyl acetoacetate (5396-89-4); Benzyl benzoate (120-51-4); Benzyl butyrate (103-37-7); Benzyl cinnamate (103-41-3); Benzyl formate (104-57-4); Benzyl hexanoate; NSC-53964 (6938-45-0); Benzyl isobutyrate (103-28-6); Benzyl isovalerate (103-38-8); Benzyl phenylacetate (102-16-9); Benzyl propionate (122-63-4); Benzyl salicylate (118-58-1); Benzyl trans-2-methyl-2-butenoate (37526-88-8); beta-Ionyl acetate (22030-19-9); beta-Naphthyl anthranilate (63449-68-3); Bornyl acetate (76-49-3); Bornyl butyrate (13109-70-1); Bornyl formate (7492-41-3); Bornyl isovalerate (endo-) (76-50-6); Bornyl valerate (7549-41-9); Butyl 10-undecenoate (109-42-2); Butyl 2-decenoate (7492-45-7); Butyl acetate (123-86-4); Butyl acetoacetate (591-60-6); Butyl butyrate (109-21-7); Butyl butyryllactate (7492-70-8); Butyl cinnamate (538-65-8); Butyl formate (592-84-7); Butyl heptanoate (5454-28-4); Butyl hexanoate (626-82-4); Butyl isobutyrate (97-87-0); Butyl isovalerate (109-19-3); Butyl levulinate (2052-15-5); Butyl phenylacetate (122-43-0); Butyl propionate (590-01-2); Butyl salicylate (2052-14-4); Butyl valerate (591-68-4); Carvyl acetate (97-42-7); Carvyl propionate (97-45-0); Cedryl acetate (77-54-3); Cinnamyl acetate (103-54-8); Cinnamyl anthranilate (87-29-6); Cinnamyl butyrate (103-61-7); Cinnamyl cinnamate (122-69-0); Cinnamyl formate (104-65-4); Cinnamyl isobutyrate (103-59-3); Cinnamyl isovalerate (140-27-2); Cinnamyl phenylacetate (7492-65-1); Cinnamyl propionate (103-56-0); cis- and trans-p-1(7),8-Menthadien-2-yl acetate (71660-03-2); cis-3-Hexen-1-yl acetate (3681-71-8); cis-3-Hexenyl anthranilate (65405-76-7); cis-3-Hexenyl benzoate (25152-85-6); cis-3-Hexenyl butyrate (16491-36-4); cis-3-Hexenyl cis-3-hexenoate (61444-38-0); cis-3-Hexenyl hexanoate (31501-11-8); cis-3-Hexenyl isobutyrate (41519-23-7); cis-3-Hexenyl lactate (61931-81-5); cis-3-Hexenyl propionate (33467-74-2); cis-3-Hexenyl salicylate (65405-77-8); cis-3-Hexenyl tiglate (67883-79-8); cis-3-Hexenyl valerate (35852-46-1); cis-3-Octenyl propionate (94134-03-9); cis-4-Decenyl acetate (67452-27-1); Citronellyl 2-methyl but-2-enoate (24717-85-9); Citronellyl acetate (150-84-5); Citronellyl anthranilate (68555-57-7); Citronellyl butyrate (141-16-2); Citronellyl formate (105-85-1); Citronellyl isobutyrate (97-89-2); Citronellyl phenylacetate (139-70-8); Citronellyl propionate (141-14-0); Citronellyl valerate (7540-53-6); Coniferan (67874-72-0); 3a,4,5,6,7,7a-hexahydro-4,7-methanoinden-6-yl acetate (5413-60-5); Tricyclodecenyl propionate (Cyclaprop) (68912-13-0); Cyclohexyl acetate (622-45-7); Cyclohexyl anthranilate (7779-16-0); Cyclohexyl butyrate (1551-44-6); Cyclohexyl cinnamate (7779-17-1); Cyclohexyl isovalerate (7774-44-9); Cyclohexyl propionate (6222-35-1); D,L-Menthol (+/−)-propylene glycol carbonate (156324-82-2); Decyl butyrate (5454-09-1); Decyl propionate (5454-19-3); Diethyl L-tartrate (87-91-2); Diethyl malate (7554-12-3); Diethyl malonate (105-53-3); Diethyl sebacate (110-40-7); Dihydrocarvyl acetate (20777-49-5); Dimethyl anthranilate (85-91-6); Dimethyl succinate (106-65-0); Dimethylbenzyl carbonyl acetate (151-05-3); Dimethylbenzyl carbinyl crotonate (93762-34-6); Dimethylbenzyl carbinyl hexanoate (891781-90-1); Dimethylbenzylcarbinyl butyrate (10094-34-5); Dimethylbenzylcarbinyl formate (10058-43-2); Dodecyl propionate (6221-93-8); Ethyl (E)-2-methyl-2-pentenoate (1617-40-9); Ethyl (p-tolyloxy)acetate (67028-40-4); Ethyl 2-acetyl-3-phenylpropionate (620-79-1); Ethyl 2-ethyl-3-phenylpropanoate (2983-36-0); Ethyl 2-ethylbutyrate (2983-38-2); Ethyl 2-ethylhexanoate (2983-37-1); Ethyl 2-methyl-3,4-pentadienoate (60523-21-9); Ethyl 2-methyl-3-pentenoate (1617-23-8); Ethyl 2-methyl-4-pentenoate (53399-81-8); Ethyl 2-methylbutyrate (7452-79-1); Ethyl 2-methylpentanoate (39255-32-8); Ethyl 2-nonynoate (10031-92-2); Ethyl 2-octenoate (7367-82-0); Ethyl 3-(2-furyl) propanoate (10031-90-0); Ethyl 3-hexenoate (2396-83-0); Ethyl 3-hydroxybutyrate (5405-41-4); Ethyl 3-hydroxyhexanoate (2305-21-1); Ethyl 3-methylpentanoate (5870-68-8); Ethyl 3-octenoate (1117-65-3); Ethyl 3-oxohexanoate (3249-68-1); Ethyl 3-phenylglycidate (121-39-1); Ethyl 3-phenylpropionate (2021-28-5); Ethyl 4-methylpentanoate (25415-67-2); Ethyl 4-phenylbutyrate (10031-93-3); Ethyl 5-hexenoate (54653-25-7); Ethyl acetate (141-78-6); Ethyl acetoacetate (141-97-9); Ethyl aconitate (mixed esters) (1321-30-8); Ethyl anthranilate (87-25-2); Ethyl benzoate (93-89-0); Ethyl benzoylacetate (94-02-0); Ethyl butyrate (105-54-4); Ethyl cinnamate (103-36-6); Ethyl cis-3-hexenoate (64187-83-3); Ethyl cis-4-heptenoate (39924-27-1); Ethyl cis-4-octenoate (34495-71-1); Ethyl cyclohexaneacetate (5452-75-5); Ethyl cyclohexanecarboxylate (3289-28-9); Ethyl cyclohexanepropionate (10094-36-7); Ethyl formate (109-94-4); Ethyl heptanoate (106-30-9); Ethyl hexanoate (123-66-0); Ethyl isobutyrate (97-62-1); Ethyl isovalerate (108-64-5); Ethyl lactate (97-64-3); Ethyl levulinate (539-88-8); Ethyl linalyl acetate (61931-80-4); Ethyl methyl-p-tolylglycidate (74367-97-8); Ethyl N-ethylanthranilate (38446-21-8); Ethyl p-anisate (94-30-4); Ethyl phenylacetate (101-97-3); Ethyl propionate (105-37-3); Ethyl pyruvate (617-35-6); Ethyl safranate (35044-59-8); Ethyl salicylate (118-61-6); Ethyl sorbate (2396-84-1); Ethyl tiglate (5837-78-5); Ethyl trans-2,cis-4-decadienoate (3025-30-7); Ethyl trans-2-butenoate (10544-63-5); Ethyl trans-2-decenoate (7367-88-6); Ethyl trans-2-hexenoate (27829-72-7); Ethyl trans-4-decenoate (76649-16-6); Ethyl undecanoate (627-90-7); Ethyl valerate (539-82-2); Ethyl vanillin isobutyrate (188417-26-7); Eugenyl formate (10031-96-6); Eugenyl isovalerate (61114-24-7); Eugenyl phenyl acetate (10402-33-2); Farnesyl acetate (29548-30-9); Floramat (67801-64-3); Fraistone (6290-17-1); Fructalate (72903-27-6); Ethyl 2-(2-methyl-1,3-dioxolan-2-yl)acetate (6413-10-1); Fruitate (80623-07-0); Furfuryl acetate (623-17-6); Furfuryl isovalerate (13678-60-9); Furfuryl pentanoate (36701-01-6); Furfuryl propionate (623-19-8); Gardocyclene (67634-20-2); Geranyl 2-methylbutyrate (68705-63-5); Geranyl acetate (105-87-3); Geranyl acetoacetate (10032-00-5); Geranyl benzoate (94-48-4); Geranyl butyrate (106-29-6); Geranyl formate (105-86-2); Geranyl hexanoate (10032-02-7); Geranyl isobutyrate (2345-26-8); Geranyl isovalerate (109-20-6); Geranyl pentanoate; Geranyl valerate (10402-47-8); Geranyl phenylacetate (102-22-7); Geranyl propionate (105-90-8); Geranyl tiglate (7785-33-3); Givescone (57934-97-1); Green acetate (Verdox) (88.41-5); Guaiacyl acetate (613-70-7); Guaiacyl phenylacetate (4112-89-4); Guaiyl acetate (134-28-1); Hedione; Kharismal; Methyl dihydrojasmonate (24851-98-7); Helvetolide (141773-73-1); Heptyl acetate (112-06-1); Heptyl butyrate (5870-93-9); Heptyl cinnamate (10032-08-3); Heptyl formate (112-23-2); Heptyl heptanoate (624-09-9); Heptyl isobutyrate (2349-13-5); Herbanate (116126-82-0); Hexyl 2-furoate (39251-86-0); Hexyl 2-methyl-3&4-pentenoate (58625-95-9); Hexyl 2-methylbutanoate (10032-15-2); Hexyl acetate (142-92-7); Hexyl benzoate (6789-88-4); Hexyl butyrate (2639-63-6); Hexyl decanoate (10448-26-7); Hexyl formate (629-33-4); Hexyl heptanoate (1119-06-8); Hexyl hexanoate (6378-65-0); Hexyl isobutyrate (2349-07-7); Hexyl isovalerate (10032-13-0); Hexyl nonanoate (6561-39-3); Hexyl octanoate (1117-55-1); Hexyl phenylacetate (5421-17-0); Hexyl propionate (2445-76-3); Hexyl salicylate (6259-76-3); Hexyl trans-2-hexenoate (33855-57-1); Isoamyl 2-furanbutyrate (7779-66-0); Isoamyl acetate (123-92-2); Isoamyl acetoacetate (2308-18-1); Isoamyl benzoate; iso-Pentyl benzoate (94-46-2); Isoamyl butyrate (106-27-4); Isoamyl cinnamate (7779-65-9); Isoamyl formate (110-45-2); Isoamyl furylpropanoate (7779-67-1); Isoamyl hexanoate, Isoamyl caproate (2198-61-0); Isoamyl isovalerate (659-70-1); Isoamyl nonanoate (7779-70-6); Isoamyl octanoate (2035-99-6); Isoamyl phenylacetate (102-19-2); Isoamyl propionate (105-68-0); Isoamyl pyruvate (7779-72-8); Isoamyl salicylate (87-20-7); Isobornyl 2-methylbutyrate (94200-10-9); Isobornyl acetate (125-12-2); Isobornyl for-mate (1200-67-5); Isobornyl isobutyrate (85586-67-0); Isobornyl isovalerate (7779-73-9); Isobornyl propionate (2756-56-1); Isobutyl 2-butenoate (589-66-2); Isobutyl acetate (110-19-0); Isobutyl acetoacetate (7779-75-1); Isobutyl angelate (7779-81-9); Isobutyl benzoate (120-50-3); Isobutyl butyrate (539-90-2); Isobutyl cinnamate (122-67-8); Isobutyl furylpropionate (105-01-1); Isobutyl heptanoate (7779-80-8); Isobutyl hexanoate (105-79-3); Isobutyl isobutyrate (97-85-8); Isobutyl isovalerate (589-59-3); Isobutyl phe-nylacetate (102-13-6); Isobutyl propionate (540-42-1); Isobutyl salicylate (87-19-4); Isoeugenyl acetate (93-29-8); Isoeugenyl formate (7774-96-1); Isoeugenyl phenylacetate (120-24-1); Isoprenyl acetate (5205-07-2); Isopropenyl acetate (108-22-5); Isopropyl 2-methylbutyrate (66576-71-4); Isopropyl benzoate (939-48-0); Isopropyl butyrate (638-11-9); Isopropyl cinnamate (7780-06-5); Isopropyl hexanoate (2311-46-8); Isopropyl isobutyrate (617-50-5); Isopropyl isovalerate (32665-23-9); Isopropyl phenylacetate (4861-85-2); Isopropyl propionate (637-78-5); Isopropyl tiglate (1733-25-1); Isopulegyl acetate (57576-09-7); (Z)-3-hexen-1-yl methyl carbonate (67633-96-9); Linalyl acetate (115-95-7); Linalyl anthranilate (7149-26-0); Linalyl benzoate (126-64-7); Linalyl butyrate (78-36-4); Linalyl cinnamate (78-37-5); Linalyl formate (115-99-1); Linalyl hexanoate (7779-23-9); Linalyl isobutyrate (78-35-3); Linalyl isovalerate (1118-27-0); Linalyl octanoate (10024-64-3); Linalyl phenylacetate (7143-69-3); Linalyl propionate (144-39-8); I-Menthyl lactate (59259-38-0); L-Monomenthyl glutarate (220621-22-7); Maltol isobutyrate (65416-14-0); Maltol propionate (68555-63-5); Menthyl acetate (16409-45-3); Menthyl isovalerate (16409-46-4); Methyl (E)-2-(Z)-4-decadienoate (4493-42-9); Methyl 1-acetoxycyclohexyl ketone (52789-73-8); Methyl 2-furoate (611-13-2); methyl 2-heptyne carbonate (111-12-6); Methyl 2-hexenoate (2396-77-2); Methyl 2-hydroxy-4-methylpentanoate (40348-72-9); Methyl 2-methylbutyrate (868-57-5); Methyl 2-methylpentanoate (2177-77-7); Methyl 2-nonenoate; NSC-76416; Neofolione (111-79-5); Methyl 2-nonynoate (111-80-8); Methyl 2-octynoate (111-12-6); Methyl 3,7-dimethyl-6-octenoate (2270-60-2); Methyl 3-hexenoate (2396-78-3); Methyl 3-hydroxyhexanoate (21188-58-9); Methyl 3-nonenoate (13481-87-3); Methyl 3-phenylpropionate (103-25-3); Methyl 4-methylvalerate (2412-80-8); Methyl 4-pentenoate (818-57-5); Methyl 4-Phenylbutyrate (2046-17-5); Methyl 9-undecenoate (5760-50-9); Methyl anisate (121-98-2); Methyl benzoate (93-58-3); Methyl butyrate (623-42-7); Methyl caproate (106-70-7); Methyl cinnamate (103-26-4); Methyl cis-4-octenoate (21063-71-8); Methyl cyclohexanecarboxylate (4630-82-4); Methyl heptanoate (106-73-0); Methyl isobutyrate (547-63-7); Methyl isovalerate (556-24-1); Methyl jasmonate (1211-29-6); Methyl nicotinate (93-60-7); Methyl nonanoate (1731-84-6); Methyl octyne carbonate (111-80-8); Methyl o-methoxybenzoate (606-45-1); Methyl phenylacetate (101-41-7); Methyl propionate (554-12-1); Methyl salicylate (119-36-8); Methyl sorbate (689-89-4); Methyl trans-2-octenoate (7367-81-9); Methyl valerate (624-24-8); Myraldyl acetate (72403-67-9); Myrtenyl acetate (1079-01-2); N,N-dimethyl menthyl succinamide (544714-08-1); n-Butyl 2-methylbutyrate (15706-73-7); Neryl acetate (141-12-8); Neryl butyrate (999-40-6); Neryl formate (2142-94-1); Neryl isobutyrate (2345-24-6); Neryl isovalerate (3915-83-1); Neryl propionate (105-91-9); n-Hexyl 2-butenoate (19089-92-0); Nonyl isovalerate (7786-47-2); Nonyl octanoate (7786-48-3); Nopyl acetate (128-51-8); Octyl acetate (112-14-1); Octyl butyrate (110-39-4); Octyl formate (112-32-3); Octyl heptanoate (5132-75-2); Octyl isovalerate (7786-58-5); Octyl octanoate (2306-88-9); Octyl phenylacetate (122-45-2); Octyl propionate (142-60-9); o-Tolyl acetate (533-18-6); o-Tolyl isobutyrate (36438-54-7); o-Tolyl salicylate (617-01-6); Oxyoctaline formate (65405-72-3); Pent-2-enyl hexanoate (74298-89-8); Perillyl acetate (15111-96-3); Phenethyl 2-furoate (7149-32-8); Phenethyl acetate (103-45-7); Phenethyl anthranilate (133-18-6); Phenethyl benzoate (94-47-3); Phenethyl butyrate (103-52-6); Phenethyl cinnamate (103-53-7); Phenethyl formate (104-62-1); Phenethyl hexanoate (6290-37-5); Phenethyl isobutyrate (103-48-0); Phenethyl isovalerate (140-26-1); Phenethyl phenylacetate (102-20-5); Phenethyl propionate (122-70-3); Phenethyl salicylate (87-22-9); Phenethyl senecioate (42078-65-9); Phenethyl tiglate (55719-85-2); Phenyl acetate (122-79-2); Phenyl ethyl pivalate (67662-96-8); Phenylethyl 2-methylbutyrate (24817-51-4); Piperonyl acetate (326-61-4); Piperonyl isobutyrate (5461-08-5); Pivacyclene (68039-44-1); Prenyl acetate (1191-16-8); Prenyl benzoate (5205-11-8); Prenyl caproate (76649-22-4); Prenyl formate (68480-28-4); Prenyl isobutyrate (76649-23-5); Propyl 2,4-decadienoate (84788-08-9); Propyl 2-furanacrylate (623-22-3); Propyl 2-furoate (615-10-1); Propyl acetate (109-60-4); Propyl benzoate (2315-68-6); Propyl butyrate (105-66-8); Propyl cinnamate (7778-83-8); Propyl heptanoate (7778-87-2); Propyl hexanoate (626-77-7); Propyl isobutyrate (644-49-5); Propyl isovalerate (557-00-6); Propyl phenylacetate (4606-15-9); Propyl p-hydroxybenzoate (94-13-3); p-Tolyl 3-methylbutyrate (55066-56-3); p-Tolyl acetate (140-39-6); p-Tolyl isobutyrate (103-93-5); p-Tolyl laurate (10024-57-4); p-Tolyl octanoate (59558-23-5); p-Tolyl phenylacetate (101-94-0); Rhodinyl acetate (141-11-7); Rhodinyl butyrate (141-15-1); Rhodinyl formate (141-09-3); Rhodinyl isobutyrate (138-23-8); Rhodinyl isovalerate (7778-96-3); Rhodinyl phenylacetate (139-70-8); Rhodinyl propionate (105-89-5); Romandolide (236391-76-7); Rose crystal (90-17-5); Salol; Salphenyl (118-55-8); Strawberry aldehyde (77-83-8); Styrallyl acetate (93-92-5); Styrallyl butyrate (3460-44-4); Styrallyl propionate (120-45-6); Terpinyl acetate (8007-35-0); Terpinyl butyrate (2153-28-8); Terpinyl cinnamate (10024-56-3); Terpinyl isovalerate (1142-85-4); Terpinyl propionate (80-27-3); Tetrahydrofurfuryl acetate (637-64-9); Tetrahydrofurfuryl butyrate (2217-33-6); Tetrahydrofurfuryl cinnamate (65505-25-1); Tetrahydrofurfuryl propionate (637-65-0); trans-2-Heptenyl acetate (16939-73-4); trans-2-Heptenyl isovalerate (253596-70-2); trans-2-Hexenyl 2-methylbutyrate (94089-01-7); trans-2-Hexenyl butyrate (53398-83-7); trans-2-Hexenyl isovalerate (68698-59-9); trans-2-Hexenyl pentanoate (56922-74-8); trans-2-Hexenyl propionate (53398-80-4); trans-2-Octen-1-yl acetate (3913-80-2); Tri-butyrin (60-01-5); Vanillin acetate (881-68-5); Vanillin isobutyrat, Isobutavan (20665-85-4); Veramoss, methyl 2,4-dihydroxy-3,6-dimethylbenzoate (4707-47-5); and Vetiveryl acetate (117-98-6), cis-9-Octadecenyl acetate (693-80-1); trans-3-Hexenyl acetate (3681-82-1); Cis-3-hexenyl acetate (3681-71-8).

Aldehydes, such as but not limited to (+/−)-4-Ethyloctanal (58475-04-0); (+/−)-trans- and cis-5-(2,2-Dimethylcyclopropyl)-3-methyl-2-pentenal (877-60-1); (2,2,3-Trimethylcyclopent-3-en-1-yl)acetaldehyde (4501-58-0); (2,4) and (3,5) and 3,6-Di methyl-3-cyclohexenylcarbaldehyde (27939-60-2); (E)-4-Nonenal (2277-16-9); (Z)-4-Dodecenal (21944-98-9); (Z)-8-Tetradecenal (169054-69-7); 1,3-p-Menthadien-7-al (1197-15-5); 2-(p-Tolyl)propionaldehyde (99-72-9); 2,4-Heptadienal (4313-03-5); 2,4-Nonadienal (6750-03-4); 2,4-Undecadienal (13162-46-4); 2,6-Dimethyloctanal (7779-07-9); 2-Decenal (3913-71-1); 2-Dodecenal (4826-62-4); 2-Ethyl-2-heptenal (10031-88-6); 2-Ethylbutyraldehyde (97-96-1); 2-Furanacrolein (623-30-3); 2-Furfurylidenebutyraldehyde (770-27-4); 2-Hydroxy-4-methylbenzaldehyde (698-27-1); 2-Isopropyl-5-methyl-2-hexenal (35158-25-9); 2-Methyl-2-octenal (73757-27-4); 2-Methyl-2-pentenal (623-36-9); 2-Methyl-3-(2-furyl)acrolein (874-66-8); 2-methyldecanal (19009-56-4); 2-Methyloctanal (7786-29-0); 2-Methylpentanal (123-15-9); 2-Methylundecanal (110-41-8); 2-Nonenal (2463-53-8); 2-Octenal (2363-89-5); 2-Phenyl-3-(2-furyl)prop-2-enal (65545-81-5); 2-Phenyl-4-pentenal (24401-36-3); 2-Phenylpropionaldehyde (93-53-8); 2-trans,4-trans-Decadienal (25152-84-5); 2-trans-4-cis-7-cis-Tridecatrienal (13552-96-0); 2-trans-4-trans-7-cis-Decatrienal (51325-37-2); 2-trans-6-cis-Dodecadienal (21662-13-5); 2-trans-6-trans-Nonadienal (17587-33-6); 2-trans-6-trans-Octadienal (56767-18-1); 2-Tridecenal (7774-82-5); 2-Undecenal (2463-77-6); 3-(5-Methyl-2-furyl) prop-2-enal; 5-Methyl-2-furanacrolein (5555-90-8); 3,7,11-Trimethyl-2,6,10-dodecatrienal (19317-11-4); 3-Hexenal (4440-65-7); 3-Methyl-2-butenal (107-86-8); 3-Methylbutyraldehyde, Isovaleraldehyde (590-86-3); 3-Methylhexanal (19269-28-4); 3-Phenyl propionaldehyde (104-53-0); 4-Ethylbenzaldehyde (4748-78-1); 4-Heptenal (6728-31-0); 4-Hydroxybenzaldehyde (123-08-0); 6-Methylheptanal (63885-09-6); 9-Octadecenal (5090-41-5); 9-Undecenal (143-14-6); 2,6,10-trimethylundec-9-enal (141-13-9); 10-undecenal (112-45-8); 2-methyl undecanal (110-41-8); alpha-Butylcinnamaldehyde (7492-44-6); alpha-Amylcinnamaldehyde (122-40-7); 2-Benzylideneheptanal (122-40-7); alpha-Hexylcinnamaldehyde (101-86-0); alpha-Methylcinnamaldehyde (101-39-3); Anisic aldehyde (123-11-5); Benzaldehyde (100-52-5); beta-Cyclocitral (432-25-7); beta-Cyclohomocitral (472-66-2); beta-Sinensal (60066-88-8); 4-t-butylbenzenepropionaldehyde (18127-01-0); Canthoxal (5462-06-6); Cinnamaldehyde (104-55-2); cis,cis-Photocitral A (55253-28-6); cis-3-Hexenal (6789-80-6); cis-4-Decenal (30390-50-2); cis-5-Octenal (41547-22-2); cis-6-Nonenal (2277-19-2); Citral (5392-40-5); Citronellal (106-23-0); Citronellal (106-23-0); Citronelloxyacetaldehyde (7492-67-3); Cortexal, p-Isopropylphenylacetaldehyde (4395-92-0); Costenal (39770-05-3); Coumarilaldehyde (4265-16-1); Cuminaldehyde (122-03-2); Cyclamen aldehyde (103-95-7); Cyclemax (7775-00-0); Cyclomyral (68738-94-3); Decanal (112-31-2); De-hydrodivanillin (2092-49-1); 4-(octahydro-4,7-methano-5H-inden-5-ylidene)butanal (30168-23-1); Ethyl vanillin (121-32-4); Ethyl vanillin (121-32-4); Floralozone (67634-15-5); 3-(3-propan-2-ylphenyl)butanal (125109-85-5); Furfural (98-01-1); Heptanal (111-71-7); Hexanal (66-25-1); Hydroxycitronellal (107-75-5); Isononyl aldehyde (5435-64-3); Jasmorange (41496-43-9); Lauric aldehyde (112-54-9); 3-(4-tert-butylphenyl)butanal (80-54-6); Lyral (31906-04-4); 3-methyl-7-propan-2-ylbicyclo[2.2.2]oct-2-ene-5-carbaldehyde (67845-30-1); 2,6-dimethylhept-5-enal (106-72-9); trans-2-dodecenal (20407-84-5); Melafleur (68991-97-9); Melozone (30772-79-3); Methoxy melonal (62439-41-2); Muguet undecadienal (54082-68-7); Myristaldehyde (124-25-4); Myrtenal (564-94-3); Nonanal (124-19-6); o-Anisaldehyde (135-02-4); Octanal (124-13-0); o-Methoxycinnamaldehyde (1504-74-1); Perillaldehyde (18031-40-8); p-Ethoxybenzaldehyde (10031-82-0); Phenylacetaldehyde (122-78-1); 3-(7,7-Dimethyl-4-bicyclo[3.1.1]hept-3-enyl)propanal (33885-51-7); Piperonal (120-57-0); p-Menth-1-ene-9-al (29548-14-9); p-Methoxy-alpha-methylcinnamaldehyde (65405-67-6); p-Methoxycinnamaldehyde (1963-36-6); p-Methylcinnamaldehyde (1504-75-2); p-Tolylacetaldehyde (104-09-6); Safranal (116-26-7); Salicylaldehyde (90-02-8); Syringaldehyde (134-96-3); Tetradec-2-enal (51534-36-2); Tetrahydro citral (5988-91-0); Tolualdehydes (mixed o,m,p) (1334-78-7); trans,trans-2,4-Dodecadienal (21662-16-8); trans,trans-2,4-Hexadienal (142-83-6); trans,trans-2,4-Octadienal (30361-28-5); trans-2,cis-6-Nonadienal (557-48-2); trans-2-Heptenal (18829-55-5); trans-2-Hexenal (6728-26-3); trans-4-Decenal (65405-70-1); trans-4-Hexenal (25166-87-4); Trifernal (16251-77-7); 2,4-dimethylcyclohex-3-ene-1-carbaldehyde (68039-49-6); Tropional (1205-17-0); Undecanal (112-44-7); Vanillin (121-33-5); Veratraldehyde (120-14-9); and Vernaldehyde (66327-54-6).

Ketones, such as but not limited to (+/−) [R-(E)]-5-Isopropyl-8-methylnona-6,8-dien-2-one (2278-53-7); (E) & (Z)-4,8-Dimethyl-3,7-nonadien-2-one (817-88-9); (E)-2-(2-Octenyl)cyclopentanone (65737-52-2); (E)-2-Nonen-4-one (27743-70-0); (E)-5-Nonen-2-one (27039-84-5); (E)-6-Methyl-3-hepten-2-one (20859-10-3); (E)-7-Methyl-3-octen-2-one (33046-81-0); (E,E)-3,5-Octadien-2-one (30086-02-3); 1-(3-(M ethylthio)-butyryl)-2,6,6-trimethylcyclohexene (68697-67-6); 1-(p-Methoxyphenyl)-1-penten-3-one (104-27-8); 1-(p-Methoxyphenyl)-2-propanone (122-84-9); 1,4-Dimethyl-4-acetyl-1-cyclohexene (43219-68-7); 1,5-Octadien-3-one (65213-86-7); 10-Undecen-2-one (36219-73-5); 1-Hydroxy-4-methyl-2-pentanone (68113-55-3); 1-Methyl-1-cyclopenten-3-one (2758-18-1); 1-Methyl-2,3-cyclohexadione (3008-43-3); 1-Octen-3-one (4312-99-6); 2-(3,7-Dimethyl-2,6-octadienyl)cyclopentanone (68133-79-9); 2,2,6-Trimethylcyclohexanone (2408-37-9); 2,3,3-Trimethylindan-1-one (54440-17-4); 2,3-Octanedione (585-25-1); 2,3-Undecadione (7493-59-6); 2,4-Dimethylacetophenone (89-74-7); 2,6,10-Trimethyl-2,6,10-petadecatrien-14-one (762-29-8); 2,6-Dimethyl-4-heptanone (108-83-8); 2-Acetyl-3,5-dimethylfuran (22940-86-9); 2-Butyrylfuran (4208-57-5); 2-Cyclohexenone (930-68-7); 2-Cyclopentylcyclopentanone (4884-24-6); 2-Decanone (693-54-9); 2-Hepten-4-one (4643-25-8); 2-Hexanoylfuran (14360-5-0); Pentyl 2-furyl ketone (14360-50-0); 2-Hexylidene cyclopentanone (17373-89-6); 2-Hydroxy-3,5,5-trimethyl-2-cyclohexenone (4883-60-7); 2-Hydroxy-5-methylacetophenone (1450-72-2); 2-Hydroxyacetophenone (118-93-4); 2-Methoxyacetophenone (4079-52-1); 2-Methylacetophenone (577-16-2); 2-Methylheptan-3-one (13019-20-0); 2-Pentadecanone (2345-28-0); 2-Pentanone (107-87-9); 2-Pentanoylfuran (3194-17-0); 2-Tridecanone (593-08-8); 3-(Hydroxymethyl)-2-heptanone (65405-68-7); 3,4-Dimethyl-1,2-cyclopentadione (13494-06-9); 3,5-Dimethyl-1,2-cyclopentadione (13494-07-0); 3-Benzyl-4-heptanone (7492-37-7); 3-Decanone (928-80-3); 3-Decen-2-one (10519-33-2); 3-Ethyl-2-hydroxy-2-cyclopenten-1-one (21835-01-8); 3-Ethyl-2-hydroxy-4-methylcyclopent-2-en-1-one (42348-12-9); 3-Heptanone (106-35-4); 3-Hepten-2-one (1119-44-4); 3-Hexanone (589-38-8); 3-Hydroxy-2-pentanone (3142-66-3); 3-hydroxy-3-methyl-2,4-nonadienone (544409-58-7); 3-Methyl-1-cyclopentadecanone (541-91-3); 3-Methyl-2-(n-pentanyl)-2-cyclopenten-1-one (1128-08-1); 3-Methyl-2,4-nonanedione (113486-29-6); 3-Methyl-4-phenyl-3-butene-2-one (1901-26-4); 3-Methylcyclohexanone (591-24-2); 3-Nonanone (925-78-0); 3-Nonen-2-one (14309-57-0); 3-Octanone (106-68-3); 3-Octen-2-one (1669-44-9); 3-Penten-2-one (625-33-2); 3-Propylidenephthalide (17369-59-4); 4-(p-hydroxyphenyl)-2-butanone (5471-51-2); 4-(p-Methoxyphenyl)-2-butanone (104-20-1); 4-(p-Tolyl)-2-butanone (7774-79-0); 4-Heptanone (123-19-3); 4-Hydroxyacetophenone (99-93-4); 4-Isopropyl-2-cyclohexenone (500-02-7); 4-Mercapto-4-methyl-2-hexanone (851768-52-0); 4'-Methyl acetophenone (122-00-9); 4-Methyl-1-phenyl-2-pentanone (5349-62-2); 4-Methyl-2-pentanone (108-10-1); 4-Methyl-3-penten-2-one (141-79-7); 4-Octen-3-one (14129-48-7); 4-Phenyl-3-buten-2-one (122-57-6); 5-Methyl-2,3-hexanedione (13706-86-0); 5-Methyl-3-hexen-2-one (5166-53-0); 5-Methyl-5-hexen-2-one (3240-09-3); 6-Methyl-3,5-heptadien-2-one (1604-28-0); 6-Methyl-5-hepten-2-one (110-93-0); 8,9-Dehydrotheaspirone (80722-28-7); 8-Nonen-2-one (5009-32-5); Acetoanisole (100-06-1); Acetophenone (98-86-2); Allyl-a-ionone, Cetone V (79-78-7); alpha-Damascone (43052-87-5); alpha-Ionone (127-41-3); Azarbre (68845-36-3); Benzoin (119-53-9); Benzophenone (119-61-9); beta-Damascone (23726-92-3); beta-Ionone (14901-07-6); Beta-isomethylionone (79-89-0); 8-methyl-1,5-benzodioxepin-3-one (28940-11-6 35783-05-2); 3-methyl-5-propylcyclohex-2-en-1-one (3720-16-9); cis-3-Nonen-1-ol (10340-23-5); cis-Jasmone (488-10-8); Citronellylacetone (4433-36-7); Claritone (74338-72-0); Cosmone (259854-70-1); Cuminone; p-Isopropylacetophenone (645-13-6); Cyclic ethylene glycol tridecanedioate, Cycloheptadeca-9-en-1-one (542-46-1); Cyclotene, Methyl cyclopentanolone (80-71-7); Damascenone (23726-93-4); d-Camphor (464-49-3); Dehydrodihydroionone (20483-36-7); Dehydronootkatone (5090-63-1); 2-pentyl cyclopentanone (4819-67-4); delta-Damascone (57378-68-4); d-Fenchone (4695-62-9); Dibenzyl ketone (102-04-5); Dihydro-alpha-ionone (31499-72-6); Dihydro-beta-ionone (17283-81-7); Dihydronootkatone (20489-53-6); dl-Camphor (21368-68-3); Dulcinyl (55418-52-5); 1-(5,5-dimethyl-1-cyclohexenyl)pent-4-en-1-one (56973-85-4); Epoxyoxophorone (38284-11-6); Ethyl vinyl ketone (1629-58-9); Exaltenone (14595-54-1); Fenchone (1195-79-5); 2-butan-2-ylcyclohexan-1-one (14765-30-1); Furfurylacetone (699-17-2); gamma-Ionone (79-76-5); Geranylacetone (3796-70-1); Gingerone (122-48-5); Hydroxyacetone (116-09-6); Iso E Super (54464-57-2); Isojasmone (11050-62-7); Isomethyl-alpha-ionone (127-51-5); Isophorone (78-59-1); Jasmatone (13074-65-2); Kephalis (36306-87-3); Keto butyraldehyde dimethyl acetal, 3-Oxobutanal dimethyl acetal (5436-21-5); Koavone (81786-73-4); L-carvone (6485-40-1); I-Fenchone (7787-20-4); Methyl beta-naphthyl ketone (93-08-3); Methyl heptyl ketone (821-55-6); Methyl hexyl ketone (111-13-7); Methyl-alpha-ionone (127-42-4); Methyl-alpha-ionone, alpha-Irone (79-69-6); Methyl-beta-ionone (127-43-5); Muscenone (82356-51-2); Nootkatone (4674-50-4); 1-Naphthalen-1-ylethanone (93-08-3);

Orivone (16587-71-6); para tert-Butylcyclohexanone (98-53-3); Paradol (27113-22-0); 2-cyclohexyl-1,6-heptadien-3-one (313973-37-4); Pinocamphone (18358-53-7); Plicatone (41724-19-0); Propiophenone (93-55-0); Pseudoionone (141-10-6); Romanone, Exaltone (502-72-7); Spirogalbanone (224031-70-3); Tetramethyl ethylcyclohexenone (mixture of isomers): 5-Ethyl-2,3,4,5-tetramethyl-2-cyclohexen-1-one and 5-Ethyl-3,4,5,6-tetramethyl-2-cyclohexen-1-one (17369-60-7); Tonalide, Fixolide (1506-02-1); trans, alpha-Damascone (24720-09-0); Trimofix 0 (144020-22-4 68610-78-6); Vanillalacetone (1080-12-2); Veloutone (65443-14-3); and Verbenone (80-57-9).

Lactones and O-heterocycles, such as but not limited to (+/−)-3-Methyl-gamma-decalactone (67663-01-8); (+/−)-Dihydromintlactone (92015-65-1); 2-(2-Hydroxy-4-methyl-3-cyclohexenyl)propionic acid gamma-lactone (57743-63-2); 2-(4-Methyl-2-hydroxyphenyl) propionic acid-gam ma-lactone (65817-24-5); 2,5-Dimethyl-3(2H)-furanone (14400-67-0); 2,5-Dimethyl-4-ethoxy-3(2H)-furanone (65330-49-6); 2,5-Dimethyl-4-methoxy-3(2H)-furanone (4077-47-8); 2-Acetyl-3,5-dimethylfuran (22940-86-9); 2-Ethyl-4-hydroxy-5-methyl-3(2H)-furanone (27538-09-6); 2-Methyltetrahydrofuran-3-one (3188-00-9); 2-Nonenoic acid gamma-lactone (21963-26-8); 2-Oxo-3-ethyl-4-butanolide (923291-29-6); 2-Undecanone (112-12-9); 3-Butylidenephthalide; 3-Butylphthalide (6066-49-5); 3-Heptyldihydro-5-methyl-2(3H)-furanone (40923-64-6); 3-Propylidenephthalide (17369-59-4); 4,4-Dibutyl-gamma-butyrolactone (7774-47-2); 4-Acetyl-2,5-dimethyl-3(2H)-furanone (36871-78-0); 4-Hydroxy-4-methyl-7-cis-decenoic acid gamma lactone (70851-61-5); 4-Hydroxy-5-methyl-3(2H)-furanone (19322-27-1); 4-Hydroxybutanoic acid lactone (96-48-0); 5,6-Beta-ionone epoxide (23267-57-4); 5-Hydroxy-2,4-decadienoic acid lactone (27593-23-3); 5-Hydroxy-2-decenoic acid lactone (51154-96-2); 5-Hydroxy-2-dodecenoic acid lactone (16400-72-9); 5-Hydroxy-4-methylhexanoic acid delta-lactone (10413-18-0); 5-Hydroxy-8-undecenoic acid delta-lactone (68959-28-4); 5-Hydroxyundecanoic acid lactone (710-04-3); 5-Methyl-3(2H)-furanone (3511-32-8); 5-Pentyl-3H-furan-2-one (51352-68-2); 6-Hydroxy-3,7-dimethyloctanoic acid lactone (499-54-7); 6-Octyltetrahydro-2H-pyran-2-one (7370-92-5); 7-Decen-4-olide (67114-38-9); 8.Decen-5-olide (32764-98-0); 9-Decen-5-olide (74585-00-5); 9-Dodecene-5-olide (15456-68-5); 9-Tetradecen-5-olide (15456-70-9); Ambrocenide (211299-54-6); Tetramethyl-2,4,5,5a,7,8,9,9b-octahydro-1H-benzo[e][1]benzofuran (6790-58-5); Anther (56011-02-0); beta-Angelica lactone (53774-21-3); Boisambrene forte (58567-11-6); Boisiris (68845-00-1); Bovolide (774-64-1); Carvone-5,6-oxide (18383-49-8); Coumarin (91-64-5); Decatone (34131-98-1); Dehydromenthofurolactone (75640-26-5); delta Hexadecalactone (7370-44-7); delta-Decalactone (705-86-2); delta-Dodecalactone (713-95-1); delta-Hexalactone (823-22-3); delta-Octadecalactone (1227-51-6); delta-Octalactone (698-76-0); delta-Tetradecalactone (2721-22-4); Dihydroactinolide; Dihydroactindiolide (15356-74-8); Dihydrocoumarin (119-84-6); Epoxyoxophorone (38284-11-6); epsilon-Decalactone (5579-78-2); epsilon-Dodecalactone (16429-21-3); Ethyl maltol (4940-11-8); Furyl propyl ketone (4208-57-5); gamma-Angelica lactone (591-12-8); gamma-Decalactone (706-14-9); gamma-Dodecalactone (2305-05-7); gam ma-Heptalactone (105-21-5); gamma-Hexalactone (695-06-7); gamma-Methyldecalactone (7011-83-8); gamma-Octadecalactone (502-26-1); gamma-Undecalactone (104-67-6); gam ma-Valerolactone (108-29-2); Hydroxynonanoic acid, delta lactone (3301-94-8); Isoambrettolide (28645-51-4); Jasmin lactone (25524-95-2); Lavender lactone (1073-11-6); Maltol (118-71-8); Norambreinolide (564-20-5); Oaklactone (39212-23-2); Octahydrocoumarin (4430-31-3); omega-6-Hexadecenlactone (7779-50-2); omega-Pentadecalactone (106-02-5); Orin Lactone (134359-15-2); Pentyl 2-furyl ketone (14360-50-0); Piperitenone oxide (35178-55-3); Gamma nonalactone (104-61-0); 4-(p-hydroxyphenyl)-2-butanone (5471-51-2); Strawberry furanone (3658-77-3); Ethylene brassylate (105-95-3); and Tuberose lactone (153175-57-6).

Ethers, acetals and ketals, such as but not limited to 2,6-Dimethyl-5-heptenal propyl-eneglycol acetal (74094-63-6); 1-(p-Methoxyphenyl)-2-propanone (122-84-9); 1,1-Dimethoxy-trans-2-hexene; trans-2-Hexenal dimethyl acetal (18318-83-7); 1-Ethoxy-3-methyl-2-butene; Prenyl ethyl ether (22094-00-4); 2,4-Dimethylanisole (6738-23-4); 2,5-Dimethyl-4-methoxy-3(2H)-furanone (4077-47-8); 2,6-Nonadienal diethyl acetal (67674-36-6); 2-Methoxy-4-propylphenol (2785-87-7); 2-Methoxy-4-vinylphenol (7786-61-0); 2-Methoxyacetophenone (4079-52-1); 2-Nonanone propyleneglycol acetal (165191-91-3); 2-Phenylpropanal propyleneglycol acetal (67634-23-5); 2-Phenylpropionaldehyde dimethyl acetal (90-87-9); 3,4-Dimethoxy-1-vinylbenzene (6380-23-0); 3-Oxobutanal dimethyl acetal (5436-21-5); 4-(p-Methoxyphenyl)-2-butanone (104-20-1); 4-Ethylguaiacol (2785-89-9); 4-Heptenal diethyl acetal (18492-65-4); 4-Methyl-2,6-dimethoxyphenol (6638-05-7); Acetaldehyde butyl phenethyl acetal (64577-91-9); Acetaldehyde diisoamyl acetal (13002-09-0); Acetaldehyde ethyl phenethyl acetal (2556-10-7); Acetaldehyde hexyl isoamyl acetal (233665-90-2); Acetaldehyde, phenethyl propyl acetal (7493-57-4); Acetoanisole (100-06-1); Acetoxy-1-ethoxyethane; (1608-72-6); alpha-Amylcinnamaldehyde dimethyl acetal (91-87-2); Ambrocenide (211299-54-6); (3aR,5aS,9aS,9bR)-3a,6,6,9a-tetramethyl-2,4,5,5a,7,8,9,9b-octahydro-1H-benzo[e][1]benzofuran (6790-58-5); Anisaldehyde diethyl acetal (2403-58-9); Anisole (100-66-3); Anisyl alcohol (105-13-5); Anisyl phenylacetate (102-17-0); Anther (56011-02-0); Benzaldehyde dimethyl acetal (1125-88-8); Benzaldehyde propylene glycol acetal (2568-25-4); Benzyl ethyl ether (539-30-0); Benzyl isoeugenol ether (120-11-6); Benzyl methoxyethyl acetal (7492-39-9); beta-Naphthyl isobutyl ether (2173-57-1); beta-Naphthyl methyl ether (93-04-9); Boisambrene forte (58567-11-6); Boisiris (68845-00-1); Butyl beta-naphtyl ether (10484-56-7); Carvacryl ethyl ether (4732-13-2); Cedroxyde (71735-79-0); Cinnamaldehyde ethylene glycol acetal (5600-60-6); Cinnamaldehyde propyleneglycol acetal (1/9/4353); Citral diethyl acetal (7492-66-2); Citral dimethyl acetal (7549-37-3); Citral glyceryl acetal (5694-82-6); Cyclohexanone diethyl ketal (1670-47-9); Decanal propyleneglycol acetal (5421-12-5); Dehydrodivanillin (2092-49-1); Dehydroxylinalool oxide (13679-86-2); Dehydrozingerone (1080-12-2); Dibenzyl ether (103-50-4); Digeranyl ether (31147-36-1); Diphenyl ether (101-84-8); Dodecanal dimethyl acetal (14620-52-1); Dulcinyl (55418-52-5); Estragole;

Isoanethole; NSC-404113 (140-67-0); Ethyl aceto-acetate ethyleneglycol ketal (10/1/6413); Ethyl linalyl ether (72845-33-1); Ethyl vanillin propylene glycol acetal (68527-76-4); Eucalyptol (470-82-6); Eugenol (97-53-0); Eugenyl methyl ether (93-15-2); Florol, Florosa (63500-71-0); Floropal (5182-36-5); Folenox (67999-56-8); Furfuryl methyl ether (13679-46-4); Gingerone; Zingerone (122-48-5); Guaiacol (90-05-1); Gyrane (24237-00-1); Heptanal propyleneglycol acetal (4351-10-4); Heptanal, dimethyl acetal (10032-05-0); Herbavert (24691-15-4); Herboxane (54546-26-8); Hexanal dihexyl acetal (33673-65-3); Hexanal hexyl isoamyl acetal (896447-13-5); Hydroxycitronellal diethyl acetal (7779-94-4); Hydroxycitronellal dimethyl acetal (141-92-4); Hydroxycitronellal propyleneglycol acetal (93804-64-9); Indoflor (18096-62-3); Isoeugenol (97-54-1); lsoeugenyl ethyl ether (7784-67-0); lsoeugenyl formate (7774-96-1); lsoeugenyl methyl ether (93-16-3); Isovaleraldehyde diethyl acetal (3842-03-3); Jasmal (18871-14-2); Karanal (117933-89-8); Leaf acetal (28069-74-1); Limetol (7392-19-0); Linalool oxide (1365-19-1); L-Menthyl methyl ether (1565-76-0); Methyl hexyl ether (4747-07-3); 6,6-dimethoxy-2,5,5-trimethylhex-2-ene (67674-46-8); Methyl phenethyl ether (3558-60-9); Myrcenyl methyl ether (24202-00-4); Nerol oxide (1786-08-9); Nonanal dimethyl acetal (18824-63-0); Nonanal propyleneglycol acetal (68391-39-9); o-(Ethoxymethyl)phenol (20920-83-6); Octanal dimethyl acetal (10022-28-3); Octanal pro-pyleneglycol acetal (74094-61-4); Okoumal (131812-67-4); o-Methylanisole (578-58-5); 0-Methylthymol; Thymol methyl ether (1076-56-8); o-Vinylanisole (612-15-7); p-Dimethoxybenzene (150-78-7); 2-methyl-4-methylidene-6-phenyloxane (30310-41-9); Phenyl acetaldehyde diethyl acetal (6314-97-2); Phenylacetaldehyde 2,3-butylene glycol acetal (5468-06-4); Phenylacetaldehyde diisobutyl acetal (68345-22-2); Phenylacetaldehyde dimethyl acetal (101-48-4); p-Methoxybenzaldehyde (123-11-5); p-Methylanisole (104-93-8); p-Propylanisole; Dihydroanethole (104-45-0); Prenyl ethyl ether (22094-00-4); Propenylguaethol (94-86-0); Propylene acetal (3390-12-3); Rhubafurane (82461-14-1); Rhubofix (41816-03-9); Rhuboflor (93939-86-7); 4-methyl-2-(2-methylprop-1-enyl)oxane (16409-43-1); Rosyrane (60335-71-9); Thymol methyl ether (1076-56-8); trans-2-Hexenal dimethyl acetal (18318-83-7); trans-2-Hexenal propylene glycol acetal (94089-21-1); trans-Anethole (4180-23-8); Valeraldehyde propyleneglycol acetal (74094-60-3); Vanillin erythro and threo-butan-2,3-diol acetal (63253-24-7); Vanillin isobutyrate; Isobutavan (20665-85-4); Vanillin propylene glycol acetal (68527-74-2); Vanillyl alcohol (498-00-0); Vanillyl ethyl ether (13184-86-6); Veratrole (91-16-7); Verdalia (53018-24-9); and Vigoflor (68480-11-5).

N- and S-compounds, such as but not limited to 2-(1-Methylpropyl)thiazole (18277-27-5); 2-(3-Phenylpropyl)pyridine (2110-18-1); 2,3-Diethylpyrazine (15707-24-1); 2,3-Dimethyl pyrazine (5910-89-4); 2,4-Dimethyl-5-acetylthiazole (38205-60-6); 2,5 or 6-Methoxy-3-methylpyrazine (mixture of isomers) (2882-22-6); 2,5-Diethyl-3-methylpyrazine (32736-91-7); 2,5-Dimethyl-3-ethylpyrazine (27043-05-6); 2,5-Dimethyl pyrazine (123-32-0); 2,6-Dimethylpyrazine (108-50-9); 2-Acetyl-3,5(and 6)-dimethylpyrazine (54300-08-2); 2-Acetyl-3-ethylpyrazine (32974-92-8); 2-Acetyl-3-methylpyrazine (23787-80-6); 2-Acetylthiazole (24295-03-2); 2-Ethyl-3-methylpyrazine (15707-23-0); 2-Ethyl-4-methylthiazole (15679-12-6); 2-Ethyl-5-methylpyrazine (13360-64-0); 2-Ethylpyrazine (13925-00-3); 2-Isobutyl-3-methoxypyrazine (24683-00-9); 2-Isobutyl-3-methylpyrazine (13925-06-9); 2-Isobutylthiazole (18640-74-9); 2-Isopropyl-4-methylthiazole (15679-13-7); 2-Isopropylpyrazine (29460-90-0); 2-Methoxy-3-(1-methylpropyl)pyrazine (24168-70-5); 2-Methoxy-3(5 and 6)-isopropylpyrazine (25773-40-4); 2-Methyl-3,5 or 6-ethoxypyrazine (32737-14-7); 2-Methyl-4-propyl-1,3-oxathiane (67715-80-4); 2-Propylpyridine (622-39-9); 3,5-Diethyl-2-methylpyrazine (18138-05-1); 3-Ethyl-2,6-dimethylpyrazine (13925-07-0); 4-Methyl-5-thiazoleethanol (137-00-8); 4-Methyl-5-thiazoleethanol acetate (656-53-1); 5H-5-Methyl-6,7-dihydrocyclopenta(b)pyrazine (23747-48-0); 6,7-Dihydro-2,3-dimethyl-5H-cyclopentapyrazine (38917-63-4); 6-Methylquinoline (91-62-3); Acetylpyrazine (22047-25-2); alpha-Terpinyl anthranilate (14481-52-8); beta-Naphthyl anthranilate (63449-68-3); Buccoxime (75147-23-8); Butanal dibenzyl thioacetal (101780-73-8); Butyl anthranilate (7756-96-9); Cinnamyl anthranilate (87-29-6); Cinnamyl nitrile (1885-38-7); cis-3-Hexenyl anthranilate (65405-76-7); Citronellyl anthranilate (68555-57-7); Citronellyl nitrile (51566-62-2); dodecanenitrile (2437-25-4); Cuminyl nitrile (13816-33-6); Cyclohexyl anthranilate (7779-16-0); Decanonitrile (1975-78-6); Dimethyl anthranilate (85-91-6); DL-(3-Amino-3-carboxypropyl)dimethylsufonium chloride (3493-12-7); Ethyl anthranilate; NSC-4146 (87-25-2); Ethyl N-ethylanthranilate (38446-21-8); Ethyl nitrite; Nitrous ethyl ether (109-95-5); Ethyl N-methylanthranilate (35472-56-1); Fleuranile (134123-93-6); Frescile (85351-07-1); Frutonile (69300-15-8); Furfuryl mercaptan (98-02-2); 3,7-dimethyloct-6-enenitrile (5146-66-7); Grapefruit mercaptan (71159-90-5); Indole (120-72-9); Isobutyl anthranilate (7779-77-3); Isobutyl N-methylanthranilate (65505-24-0); Isopropyl quinoline (137-79-5); Isoquinoline (119-65-3); Labienoxime (81783-01-9); Lemonile (61792-11-8); Linalyl anthranilate (7149-26-0); Methoxypyrazine (3149-28-8); Methyl 3-methylthiopropionate (13532-18-8); Methyl anthranilate (134-20-3); Methyl N,N-dimethylanthranilate; NSC-97545 (10072-05-6); Methyl N-acetylanthranilate (2719-08-6); Methyl N-formylanthranilate (41270-80-8); Methyl nicotinate (93-60-7); Isobutylquinoline (93-19-6); Methyl-propyl-quinoline (93-19-6); N1-(2-methoxy-4-methylbenzyl)-N2-(2-(pyridin-2-yl)ethyl)oxalamide (745047-97-6); N-Ethyl-2-isopropyl-5-methylcyclohexanecarboxamide; WS-3 (39711-79-0); (2R,4S)-2-methyl-4-propyl-1,3-oxathiane (59323-76-1); Ozonyle (22629-49-8); 2-cyclohexylidene-2-phenylacetonitrile (10461-98-0); Phenethyl anthranilate (133-18-6); Piperine (94-62-2); Propylpyrazine (18138-03-9); Skatole (83-34-1); Sodium 2-oxo-3-phenylpropionate (114-76-1); Stemone (22457-23-4); Thiogeraniol (39067-80-6); Thiomenthone (38462-22-5); and Trithioacetone (828-26-2); Nona-2,6-dienenitrile (67019-89-0).

Hydrocarbons and terpenes, such as but not limited to (1S*,4R*)-2,2-Dimethyl-3-methylene-bicyclo[2.2.1]heptane (79-92-5); (1S*,5S*)-2,6,6-Trimethyl-bicyclo[3.1.1]hept-2-ene (80-56-8); (1S*,5S*)-6,6-Dimethyl-2-methylene-bicyclo[3.1.1]heptane (127-91-3); (1S,8aR)-1,4,4,6-tetramethyl-2,3,3a,4,5,8-hexahydro-1H-5,8a-methanoazulene (11028-42-5); (3E,6E)-3,7,11-

Trimethyl-dodeca-1,3,6,10-tetraene (502-61-4); (3R,3aR,8R,8aS)-4,4,8-trimethyl-9-methylenedecahydro-3,8-methanoazulene (475-20-7); (3R,4aS,5R)-3-Isopropenyl-4a,5-dimethyl-1,2,3,4,4a,5,6,7-octahydro-naphthalene (4630-07-3); (4aS,8S,8aS)-4,4,8a-trimethyl-7-methylidene-8-(3-methylidenepent-4-enyl)-2,3,4a,5,6,8-hexahydro-1H-naphthalene (511-02-4); (E)-(1R,9S)-4,11,11-Tri methyl-8-methylene-bicyclo[7.2.0]undec-4-ene (87-44-5); (E)-3,7-dimethylocta-1,3,6-triene (13877-91-3); (E)-3,7-Dimethyl-octa-1,3,6-triene (13877-91-3); (R)-4-Isopropenyl-1-methyl-cyclohexene (5989-27-5); 1-Isopropyl-4-methyl-cyclohexa-1,3-diene (99-86-5); 1-Isopropyl-4-methyl-cyclohexa-1,4-diene (99-85-4); 1-methyl-4-propan-2-yl-cyclohexa-1,3-diene (99-86-5); 1-methyl-4-propan-2-ylcyclohexa-1,4-diene (99-85-4); 1-Methyl-naphthalene (90-12-0); 1-Octene (111-66-0); 3,7,7-Trimethyl-bicyclo[4.1.0]hept-3-ene (13466-78-9); 4-[1,5-Dimethyl-hex-4-enylidene]-1-methyl-cyclohexene (495-62-5); 4-Isopropylidene-1-methyl-cyclohexene (586-62-9); 4-methylidene-1-propan-2-ylbicyclo[3.1.0]hexane (3387-41-5); 5-Isopropyl-2-methyl-cyclohexa-1,3-diene (99-83-2); Limonene (138-86-3, 7705-14-8); 7-Methyl-3-methyl-ene-octa-1,6-diene (123-35-3); p-Cymene (99-87-6); Undeca-1,3,5-triene (16356-11-9); and undeca-1,3,5-triene (16356-11-9).

Essential oils, such as but not limited to Citronella essential oils; Clary sage essential oils; Clove essential oils; *Eucalyptus* essential oils; *Galbanum* essential oils; Geranium essential oils; Jasmin absolute, Lemon essential oils; Neroli essential oils; Orange essential oils; Osmanthus absolute; Patchouli essential oils; Peppermint essential oils; Petitgrain essential oils; Spearmint essential oils; Vetiver essential oils; and Ylang-Ylang essential oils.

In the above lists, the number in parenthesis is the CAS number of the corresponding molecule. Multifunctional fragrance molecules may appear only once or several times in the lists.

The present invention works particularly well when the complexed fragrance is a powerful fragrance.

In the context of the present invention, powerful fragrances are fragrances having high odour strength, so that they may be used in minute quantities while still providing noticeable effect. The intensity of odours is generally measured by using the Labelled Magnitude Scale (LMS), a definition of which can be found in Green B G, Shaffer G S and Gilmore M M 1993, Derivation and evaluation of a semantic scale of oral sensation magnitude with apparent ratio properties, Chemical Senses. 18(6):683-702. For odours, the scale encompasses the following strength attributes: Barely Detectable, Weak, Moderate, Strong, Very Strong and Strongest Imaginable. Powerful fragrances are typically perceived as Strong to Very Strong when dilute at 10% by weight in a solvent, such as ethanol or dipropylene glycol.

It will be understood to those skilled in the art that fragrances being perceived as Moderate, but having known malodour counteracting properties, such as terpenes, terpene alcohols and analogues, terpene esters and analogues, salicylates and cyclenes, may also be very suitable for the sake of the present invention.

Hence, in one embodiment, the pro-fragrance composition comprises one or more fragrance molecules selected from, but not limited to:

(Z)-4-Dodecenal (21944-98-9); 1-Octen-3-ol (3391-86-4); 2,6-nonadienol (28069-72-9); 2-Isobutyl-3-methoxy-pyrazine (24683-00-9); 2-Nonenal (2463-53-8); 2-Undecenal (2463-77-6); trans-4-Decenal (65405-70-1); 8-Decen-5-olide (32764-98-0); 9-Decenol (13019-22-2); Acetaldehyde, phenethyl propyl acetal (7493-57-4); 2,6,10-trimethylundec-9-enal (141-13-9); 10-undecenal (112-45-8); 2-methyl undecanal (110-41-8); Allyl amyl glycolate (67634-00-8); Allyl hexanoate (123-68-2); Allyl phenoxyacetate (7493-74-5); alpha-Amylcinnamaldehyde, alpha-Damascone (43052-87-5); 3a,6,6,9a-tetramethyl-2,4,5,5a,7,8,9,9b-octahydro-1H-benzo[e][1]benzofuran (6790-58-5); 2-Benzylideneheptanal (122-40-7); 1-(2-Tert-butylcyclohexyl)oxybutan-2-ol (139504-68-0); Amyl salicylate (2050-08-0); Anisaldehyde diethyl acetal (2403-58-9); Anisic aldehyde (123-11-5); Benzaldehyde (100-52-5); Benzyl acetate (140-11-4); beta-Naphthyl methyl ether (93-04-9); ethyl 6-(acetyloxy)hexanoate (104986-28-9); beta-Damascone (23726-92-3); beta-Ionone (14901-07-6); 4-t-butylbenzenepropionaldehyde (18127-01-0); 8-methyl-1,5-benzodioxepin-3-one (28940-11-6 35783-05-2); 3-methyl-5-propylcyclohex-2-en-1-one (3720-16-9); cis-3-Hexen-1-ol (928-96-1); cis-6-Nonenal (2277-19-2); Citral (5392-40-5); Citronellal (106-23-0); Citronellol (106-22-9); Citronellyl oxyacetaldehyde (7492-67-3); dodecanenitrile (2437-25-4); Coumarin (91-64-5); 2-trans, 6-cis-nonadienol (7786-44-9); Damascenone (23726-93-4); 2-pentyl cyclopentanone (4819-67-4); delta-Damascone (57378-68-4); Dihydro myrcenol (18479-58-8); Dimethylbenzyl carbinyl acetate (151-05-3); Diphenyl ether (101-84-8); 4-(octahydro-4,7-methano-5H-inden-5-ylidene)butanal (30168-23-1); 1-(5,5-dimethyl-1-cyclohexenyl)pent-4-en-1-one (56973-85-4); (Z)-3-methyl-5-(2,2,3-trimethyl-1-cyclopent-3-enyl)pent-4-en-2-ol (67801-20-1); Ethyl 2-methylbutyrate (7452-79-1); Ethyl 2-methylpentanoate (39255-32-8); Ethyl butyrate (105-54-4); Ethyl N-ethylanthranilate (38446-21-8); Ethyl trans-2,cis-4-decadienoate (3025-30-7); Ethyl vanillin (121-32-4); Ethyl vinyl ketone (1629-58-9); Eucalyptol (470-82-6); Eugenol (97-53-0); methyl 2,4-dihydroxy-3,6-dimethylbenzoate (4707-47-5); Farnesene (alpha and beta) (502-61-4); Fixolide (1506-02-1); Tricyclodecenyl propionate (68912-13-0); 3-(3-propan-2-ylphenyl)butanal (125109-85-5); 2-butan-2-ylcyclohexan-1-one (14765-30-1); Ethyl 242-methyl-1,3-dioxolan-2-yl)acetate (6413-10-1); gamma-Decalactone (706-14-9); gamma-Undecalactone (104-67-6); Geranyl acetate (105-87-3); 3,7-dimethyloct-6-enenitrile (5146-66-7); Hexyl salicylate (6259-76-3); Isoamyl acetate (123-92-2); Isobutyl angelate (7779-81-9); Isobutyl-quinoline (93-19-6); Isoeugenol (97-54-1); Isomethyl-alpha-ionone (127-51-5); Isopropyl quinoline (137-79-5); Tricyclodecenyl acetate (5413-60-5); 1-methyl-2-1,2,2-trimethyl-3-bicyclo[3.1.0]hexanyl]methyl]cyclopropyl]methanol 198404-98-7); L-carvone (6485-40-1); (Z)-3-hexen-1-yl methyl carbonate (67633-96-9); 3-(4-tert-butylphenyl)butanal (80-54-6); Limonene (138-86-3, 7705-14-8); Linalool (78-70-6); 3-methyl-7-propan-2-ylbicyclo[2.2.2]oct-2-ene-5-carbaldehyde(67845-30-1); 2,6-dimethylhept-5-enal (106-72-9); trans-2-dodecenal (20407-84-5); Methyl cinnamate (103-26-4); Mayol (5502-75-0); methyl 2-heptyne carbonate (111-12-6); Methyl hexyl ketone (111-13-7); Methyl octyne carbonate (111-80-8); 6,6-dimethoxy-2,5,5-trimethylhex-2-ene (67674-46-8); Methyl salicylate (119-36-8); Nerol oxide (1786-08-9); Octanal (124-13-0); 1-Naphthalen-1-ylethanone (93-08-3); (2R,4S)-2-methyl-4-propyl-1,3-oxathiane (59323-76-1); 2-cyclohexylidene-2-phenylacetonitrile (10461-98-0); 2-methyl-4-methylidene-6-phenyloxane (30310-41-9); 2-cyclohexyl-1,6-heptadien- 3-one (313973-37-4); Phenyl ethyl alcohol (60-12-8); 2-Phenoxy ethanol (122-99-6); 347,7-Dimethyl-4-bicyclo [3.1.1]hept-3-enyl)propanal (33885-51-7); (E)-3,3-Dimethyl-5-(2,2,3-trimethyl-3-cyclopenten-1-yl)-4-penten-2-ol (107898-54-4); gamma-nonalactone (104-61-0); p-Tolyl phenylacetate (101-94-0); (E)-2-ethyl-4-(2,2,3-trimethyl-1-cyclopent-3-enyl)but-2-en-1-ol (28219-61-6); 4-(p-hydroxyphenyl)-2-butanone (5471-51-2); 4-methyl-2-(2-methylprop-1-enyl)oxane (16409-43-1); m-(isocamphyl-5) cyclohexanol (66068-84-6); trans-2, cis-6-Nonadienal (557-48-2); trans-2-Hexenal (6728-26-3); trans-2-Hexenyl 2-methylbutyrate (94089-01-7); trans-Anethole (4180-23-8); 2,4-dimethylcyclohex-3-ene-1-carbaldehyde (68039-49-6); Trimofix 0 (144020-22-4 68610-78-6); Undeca-1,3,5-triene (16356-11-9); 4-methyldec-3-en-5-ol (81782-77-6); Vanillin (121-33-5); decahydrospiro(furan-2(3H),5'-(4,7) methano(5H)indene) (68480-11-5); and Nona-2,6-dienenitrile (67019-89-0);

and/or one or more essential oils selected from, but not limited to:

Citronella essential oils; Clary sage essential oils; Clove essential oils; *Eucalyptus* essential oils; *Galbanum* essential oils; Geranium essential oils; Jasmin absolutes, Lemon essential oils; Neroli essential oils; Orange essential oils; Osmanthus essential oils; Patchouli essential oils; Peppermint essential oils; Petitgrain essential oils; Spearmint essential oils; Vetiver essential oils; and Ylang-Ylang essential oils.

Other example of fragrance molecules and essential oils, including powerful fragrance molecules and essential oils may be found in "The Good Scents Company" web site (http://www.thegoodscentscompany.com).

The pro-fragrance compositions of the invention may contain only one of the fragrance molecules described herein. Alternatively, the pro-fragrance compositions may contain a mixture of two or more of the fragrance molecules described herein, for example, to create a perfume accord or a full perfume.

If more than one fragrance molecule is to be used in the pro-fragrance composition, then the fragrance molecules can be present in any proportions. Generally, the concentration of each of the fragrance molecules used will depend on the desired odour profile of the resulting pro-fragrance composition. For example, the pro-fragrance composition may be designed to produce a nice smell, or a particular odour impression that the perfumer wishes to achieve.

A perfume accord is a simplified perfume formula having a characteristic odour, such as for example a citrus odour, which is reminiscent of a lemon or a mandarin, a floral odour, which is reminiscent of a rose, a tuberose or carnation, a hesperidic odour, a woody odour, and the like.

A full perfume is a complex creation extending the odour complexity of a given accord, or combining different accords to provide a complex and hedonically pleasant sensory experience.

In this context, the applicant has found that by using a distribution of cucurbiturils, i.e. a mixture of CB[n] wherein the mixture comprises at least two different cucurbituril selected from CB[5], CB[6], CB[7] and CB[8], the odour profile desired by the perfumer is better preserved compared to when only one specific single-sized cucurbituril is used in the pro-fragrance composition The fragrance in the pro-fragrance composition exists in equilibrium between free and complexed fragrance molecules. Therefore not all of the fragrance molecules in the composition will necessarily be bound to cucurbituril. The composition will comprise free, uncomplexed fragrance molecules if the number of fragrance molecules is higher than the number of available, uncomplexed cucurbituril.

In one embodiment, the weight ratio of cucurbituril to fragrance is in the range of 1:0.01 to 1:0.9, more particularly 1:0.05 to 1:0.6, and more particularly 1:0.1 to 1:0.4.

Complex Formation

A complex of cucurbituril with a fragrance may be prepared by contacting a liquid fragrance or a fragrance solution in an appropriate solvent with the cucurbit[n]uril mixture. This may be done by any means known in the art, for example by mixing, blending, kneading, and the like. In some instances, the formation of the complex may be achieved without the need for a solvent, and the cucurbituril and the fragrance may be mixed substantially free of other components.

Alternatively, a complex of cucurbituril and the fragrance may be prepared by exposing the cucurbit[n]uril mixture to fragrance vapours.

At room temperature cucurbiturils are typically solids. Where the fragrance is also a solid, the cucurbituril and the fragrance may be dry mixed to form the complex.

Fragrance Release

The composition of the invention remains substantially odourless whilst the fragrance molecule is in complex with the cucurbituril.

The decomplexation of the pro-fragrance complex may be achieved by the action of a trigger mechanism or stimulus which then releases the fragrance. Suitable trigger mechanisms include exposure to moisture or liquid water, evaporation, heat and molecular exchange. These trigger mechanisms are effective for compositions in the condensed state, for example in solutions or in dispersions, and also in the gas state.

The terms "trigger" and "stimulus" or "stimuli" are used interchangeably throughout.

In one embodiment, the trigger is water activity. The water activity in a system is increased by increasing ambient relative humidity, the effect of which is to increase the level of moisture in the system. For example, increasing the relative humidity of the environment surrounding a pro-fragrance complex will increase the level moisture level in the immediate vicinity of said complex. The water activity may increase in such extent that water molecules will tend to bind to the cucurbiturils and displace part the fragrance molecules into the air. Contacting the pro-fragrance complex with water is another way to increase the water activity of the system.

In another embodiment, the release of the fragrance from pro-fragrances dissolved or suspended in an aqueous phase may be further controlled by controlling the ionic strength or the pH of said aqueous phase. In particular alkali cations may bind to cucurbituril and lower the binding constant of guest molecules, which are therefore released to the environment.

In another embodiment, the trigger is evaporation or heat. Evaporation and heat are related to each other via the well-known temperature dependence of the vapour pressure. When the interplay of evaporation and heat is taken as the driving force for fragrance release, the selection of the fragrances to be included in the cucurbiturils may be achieved by considering the vapour pressure of the fragrance. For example, for slow release at room temperature, fragrances having vapour pressure being higher than 0.1 mm Hg at 20° C. may be chosen, while under heat-induced release conditions, for example at 100° C. or more, fragrances having lower vapour pressure may offer better results. The person skilled in the art will appreciate the diversity of fragrances in terms of vapour pressures and odour characteristics that are left open to creation, when considering evaporation and heat as triggers.

The cucurbituril complexes described herein are capable of hosting a variety of different molecules. Molecular exchange-mediated release of fragrances from cucurbituril-based pro-fragrances is made possible due to the essential observation of the applicant that fragrance-cucurbituril complexes, and especially complexes where the guest fragrance comprises oxygen heteroatoms, are generally weak compared to the complexes involving nitrogen-containing or sulphur-containing guests, or more particularly cationic guests.

Hence, in a further embodiment, the pro-fragrance composition comprising one or more fragrance and a distribution of cucurbituril CB[n] is contacted with a trigger substance selected from metal ions and neutral, cationogen, zwitterionic, amphoteric and/or cationic nitrogen-containing, sulphur-containing and/or oxygen-containing substances. The contact between the pro-fragrance composition and the trigger may be achieved by a variety of means. For example, the pro-fragrance and the trigger may be supplied in a water-soluble or water-dispersible solid form, such as a powder or granulate. When dissolved or dispersed in water, the trigger is released and is available for triggering the fragrance release by molecular exchange. Alternatively, in-situ formation of the trigger species may occur following a change of pH.

Typical triggers include sulfonium derivatives and S-heterocyclic materials, amines and polyamines, and their quaternized forms; imines and polyimines, such as polyethyleneimines and other polyalkylene-imines, and their quaternized forms; amino-silicones, such as aminoalkyl-dimethicone; hydroxy amines; cationic surfactants, such as alkylammonium surfactants having one or two alkyl chain comprising from about 16 to about 22 carbon atoms and two to three alkyl moieties having chain length from 1 to about 4 carbon atoms, optionally having one or more hydroxyl group, or hydroxyalkyl moieties having about 1 to about 10 ethylene oxide moieties; N-heterocyclic materials, such as oxazoline derivatives, piperazine derivatives, pyridine, bipyridin and polypyridin derivatives, amino-pyridinium derivatives, cyclam derivatives, pyrrole derivatives, imidazole derivatives, and the like, and mixture thereof; fused polycyclic materials comprising said N-heterocyclic materials and mixture thereof.

In a further embodiment, the trigger is a malodour or a mixture of malodours. The malodour molecule complexes with the cucurbituril and displaces the fragrance molecule. This results in suppression of malodour by not only the release of fragrance but also by masking of the malodour through the formation of a malodour-cucurbituril complex. In particular, the molecular exchange of the fragrance molecule with the malodour molecule takes place in humid conditions.

The malodour may be selected from, but not limited to, the following list: Allyl amine; Methyl amine; Ethyl amine; Cyclobutyl amine (cyclobutanamine, urine), Cyclopentyl amine (cyclopentanamine); Cyclohexyl amine (cyclohexanamine); Cycloheptyl amine (cyclobutanamine); Isopropylamine; Butylamine; Dibu-tylamine (N-Butyl-1-butanamin); Dimethyl ethanolamine (2-(Dimethylamino) ethanol); Methyl ethanolamine (2-(Methylamino)ethanol); Diethyl ethanolamine (2-(Diethylamino)ethanol); Diethylamine (N-methylethanamine, fishy); Dipropyl amine (N-Propyl-1-propanamine); Diiso-propylamine (N-Isopropyl-2-propanamine); Dimethyl acetamide (N,N-Dimethylacetamide); Ethyl methylamine (N-Methylethanamine); Ethyl propylamine (N-ethylpropanamide); Trimethyl amine (fishy); Triethylamine (fishy); Ethylene diamine (1,2-ethanediamine, musty ammoniacal); Propylene diamine (1,3-propanediamine); tetramethylenediamine (1,4-butanediamine, Putrescine, foul); Ethylene imine (Aziridine, ammoniacal); Morpholine (fishy); Ethyl morpholine (4-ethylmorpholine, sour); Pyrrolidine (semen); Methyl ethyl pyridine (2-Ethyl-3-methylpyridine); Pyridine (burnt, sickening); Vinyl pyridine (4-vinylpyridie, nauseating); Skatole (3-methylindole, faecal); Indole (faecal); Cadaverine (Pentane-1,5-diamine, putrid); Hydrogen sulphide (rotten egg); Allyl disulphide (3-(Allyldisulfanyl)-1-propene, garlic); Ethyl isothiocyanate (isothiocyanatoethane; pungent, mustard, garlic); Ally isothiocyanate (3-isothiocyanatoprop-1-ène, sulphurous); Allyl mercaptan (2-Propene-1-thiol, garlic, sulphurous); Allyl sulphide (3-(Allylsulfanyl)-1-propene; sulphurous); Diallyl sulphide (3-(Allylsulfanyl)-1-propene; sulphurous); Dimethyl disulphide ((methylsulfanyl)ethane, unpleasant, garlic); Dimethyl trisulphide (Dimethyltrisulfane, foul); Diethyl sulphide ((Ethylsulfanyl)ethane, sulphurous); Butyl sulphide (1-(Butylsulfanyl)butane, garlic, violet); Diethyl trisulfide (Diethyltrisulfane, foul, garlic); Ethyl methyl disulphide ((methylsulfanyl)ethane, sulphurous); Phenyl sulphide (1,1'-sulfanediyldibenzene, sulphurous); Ethyl mercaptan (1.ethanethiol, sulphurous); Amyl mercaptan (1-Pentanethiol); Isoamyl mercaptan (3-methylbutane-1-thiol; sulphurous, oinion); Butyl mercaptan (1-Butanethiol, skunk-like); Isobutyl mercaptan (2-methylpropane-1-thiol, sulphurous, mustard); Dodecyl mercaptan (1-dodecanethiol); Carbon disulphide (Methanedithione, disagreeable, sweet); Dimethyl trithiocarbonate (Dimethyl carbonotrithioate); Thiophenol mercaptan; and the like.

The term "malodour" refers to unpleasant odours which are frequently encountered in everyday life and have a variety of origins. Typical malodours include odours that emanate from uncontrolled industrial activity, from human and pet body such as perspiration and excretion, from kitchen and food processing, from tobacco smoke, and from mould. Some of the most disturbing malodour for the human being are sweat; faecal; urine; wet pet; cooking odours, especially garlic, cabbage, fish and onion; and the like. Malodours may also emanate from the fatty acid and fatty acid derivatives present in consumer products, for example in soaps, detergents, shampoos, and conditioners. Other examples of particularly undesirable malodours are those produced by depilatory creams (sulphur compounds). All of these malodours are particularly pungent.

The mixture of cucurbiturils may be used to counteract a broad range of malodour molecules.

In the context of the present invention, the term "malodour counteraction" or "malodour counteracting" is considered as equivalent to "malodour suppression", "malodour mitigation" or "malodour neutralization". The result is a significant decrease of the intensity of the malodour perception by any person exposed to the source of the malodour. The intensity of odours is generally measured by using the Labelled Magnitude Scale (LMS), a definition of which can be found in Green BG, Shaffer GS and Gilmore MM 1993, Derivation and evaluation of a semantic scale of oral sensation magnitude with apparent ratio properties, Chemical Senses. 18(6):683-702. For odours, the scale encompasses the following strength attributes: Barely Detectable, Weak, Moderate, Strong, Very Strong and Strongest Imaginable. In the context of the present invention, a "significant decrease"

means that the intensity attribute of the malodour, after application of the cucurbiturils, is Weak or Barely Detectable.

Alternatively, a linear scale may be used, extending for example from 0 (no intensity perceived) and 10 (highest intensity perceived).

Odour intensity scores are preferably obtained by a panel of several people.

Pro-Fragrance Composition

The pro-fragrance compositions of the invention may further comprise uncomplexed, fragrance-free cucurbituril.

In one embodiment, the fragrance-free cucurbituril is CB[5]. CB[5] has a small cavity and is therefore substantially free of bound fragrance. This feature therefore makes it especially useful in malodour counteracting. It is believed that this smaller cucurbituril, which has a cavity volume of 82 Angström$^3$, preferably binds small gaseous malodours, such as acetylene, hydrogen sulphide and carbon disulphide.

Larger malodour molecules comprising N- and S-heteroatoms preferably bind to larger pro-fragrance cucurbiturils (e.g. CB[7] and CB[8]), and thereby release the fragrance from the pro-fragrance complex by guest exchange, as mentioned above. Pro-fragrance compositions comprising larger pro-fragrance cucurbiturils are therefore especially efficient for the reduction of malodours of N- or S-containing compounds. Nitrogen atom- and sulphur atom-containing malodour molecules are listed hereinabove and include for example Allyl amine; Methyl amine; Ethyl amine; Cyclobutyl amine (cyclobutanamine, urine), Cyclopentyl amine (cyclopentanamine); Cyclohexyl amine (cyclohexanamine); Cycloheptyl amine (cyclobutanamine); Isopropylamine; Butylamine; Dibutylamine (N-Butyl-1-butanamin); Dimethyl ethanolamine (2-(Dimethylamino) ethanol); Methyl ethanolamine (2-(Methylamino)ethanol); Diethyl ethanolamine (2-(Diethylamino)ethanol); Diethylamine (N-methylethanamine, fishy); Dipropyl amine (N-Propyl-1-propanamine); Diisopropylamine (N-Isopropyl-2-propanamine); Dimethyl acetamide (N,N-Dimethylacetamide); Ethyl methylamine (N-Methylethanamine); Ethyl propylamine (N-ethylpropanamide); Trimethyl amine (fishy); Triethylamine (fishy); Ethylene diamine (1,2-ethanediamine, musty ammoniacal); Propylene diamine (1,3-propanediamine); tetramethylenediamine (1,4-butanediamine, Putrescine, foul); Ethylene imine (Aziridine, ammoniacal); Morpholine (fishy); Ethyl morpholine (4-ethylmorpholine, sour); Pyrrolidine (semen); Methyl ethyl pyridine (2-Ethyl-3-methylpyridine); Pyridine (burnt, sickening); Vinyl pyridine (4-vinylpyridie, nauseating); Hydrogene sulphide (rotten egg); Allyl disulphide (3-(Allyldisulfanyl)-1-propene, garlic); Ethyl isothiocyanate (isothiocyanatoethane, pungent, mustard, garlic); Ally isothiocyanate (3-isothiocyanatoprop-1-ène, sulphurous); Allyl mercaptan (2-Propene-1-thiol, garlic, sulphurous); Allyl sulphide (3-(Allylsulfanyl)-1-propene; sulphurous); Diallyl sulphide (3-(Allylsulfanyl)-1-propene; sulphurous); Dimethyl disulphide ((methylsulfanyl)ethane, unpleasant, garlic); Dimethyl trisulphide (Dimethyltrisulfane, foul); Diethyl sulphide ((Ethylsulfanyl)ethane, sulphurous); Butyl sulphide (1-(Butylsulfanyl)butane, garlic, violet); Diethyl trisulfide (Diethyltrisulfane, foul, garlic); Ethyl methyl disulphide ((methylsulfanyl)ethane, sulphurous); Phenyl sulphide (1,1'-sulfanediyldibenzene, sulphurous); Ethyl mercaptan (1.ethanethiol, sulphurous); Amyl mercaptan (1-Pentanethiol); Isoamyl mercaptan (3-methylbutane-1-thiol; sulphurous, onion); Butyl mercaptan (1-Butanethiol, skunk-like); Isobutyl mercaptan (2-methylpropane-1-thiol, sulphurous, mustard); Dodecyl mercaptan (1-dodecanethiol); Carbon disulphide (Methanedithione, disagreeable, sweet); Dimethyl trithiocarbonate (Dimethyl carbonotrithioate); Thiophenol mercaptan; and the like.

In addition to the fragrance-cucurbituril complexes described herein, which optionally further comprise fragrance-free cucurbituril, the pro-fragrance compositions of the invention may also include one or more additives known to those skilled in the art.

In one embodiment, the pro-fragrance composition further comprises one or more additives selected from preservatives, dyes, pigments, sequestrants and antioxidants.

The cucurbituril-based pro-fragrance composition of the present invention can be provided in a multitude of forms and formats. In a particular embodiment, the pro-fragrance composition may be provided in powder form, in solution or as a dispersion in a liquid, in a super-critical liquid or as a compressed gas, adsorbed on a substrate, for example on a fabric, a non-woven pad, an adsorbent, and the like, or in spray form.

The pro-fragrance composition may also be added to a product, such as a consumer product for laundry care, home care or personal care. These consumer products may be in the form of powders or granulates, tablets or single-dose units, dispersions, emulsions, micro-emulsions or solutions, a hydro-alcoholic product, wipes or sponges, aerosols or liquid dispensers, creams, balsam, polish, waxes, and the like. Methods of incorporating the present composition into these different forms are well known to the person skilled in the art.

The consumer product may be a detergent, a cleansing composition, a shampoo, a softener, a softener sheet, a conditioner, a refresher, an air freshener, a deodorizing composition, a personal deodorant, an antiperspirant, a cosmetic product, a fine fragrance, a body mist, a candle, a hard surface cleaner, a cleansing wipe or mop, a soap, a styling gel, a humidity absorber, an air filtration device, a finishing product, a diaper or sanitary product, and the like.

The pro-fragrance composition may also be used to provide fragrance and malodour counteracting properties to textiles, to functional textiles and to textile finishing product; to air and various materials, such as paper, wood, plastics, stone, ceramics, metals, metal wool, wool, fibres, foams, filter material, absorbents, adsorbents, plasters, paints, inks, and the like.

The pro-fragrance compositions described herein may also be admixed with or incorporated into a perfume oil, before addition to a product. A perfume oil is a composition of substantially uncomplexed fragrance molecules. The fragrance molecules of the perfume oil are not complexed with the cucurbiturils prior to admixing or incorporating the pro-fragrance composition with or to this oil. Uncomplexed fragrance molecules may be selected from a broad range of fragrances, as mentioned herein above. For example, in a first step, the pro-fragrance composition may be prepared by complexing one or more powerful fragrances with cucurbituril and, in a second step, the pro-fragrance composition may be added to a conventional perfume oil. A mixture comprising perfume oil and the pro-fragrance composition of the present invention may comprise un-complexed fragrance molecules.

If the pro-fragrance composition is added to a perfume oil, the resulting mixture may then be microencapsulated by any methods known to the art, such as by spray drying, spray granulation, matrix particle formation, core-shell encapsulation, and the like.

Certain aspects and embodiments of the invention will now be illustrated by way of example and with reference to the figures described above.

EXPERIMENTAL AND RESULTS

Example 1 Fragrance Complex Formation and Moisture-Induced Release

A series of pro-fragrance compositions were prepared by complexing powerful fragrance molecules with a mixture of cucurbiturils, referred to as CB[n] in the following. The composition of the CB[n] mixture was 15% by weight of CB[5], 48% by weight of CB[6], 25% by weight of CB[7] and 12% by weight of CB[8]. The complexing procedure was carried out by adding 100 μL (1.25% weight in ethanol/water mixture) of each odour molecule to a glass slide coated with 100 μL (10% weight in water) of CB[n] that had been dried prior to the addition of the pro-fragrance composition. After 5 h equilibration in open space and at room temperature, the glass slide was placed in empty 500 mL flasks having pre-set relative humidity. Different relative humidity (RH) levels were obtained by previously introducing in the flask a small vessel containing a saturated salt solution in water (so-called salt hygrostat method). The following salts were used: magnesium nitrate in water (55% RH), sodium chloride in water (75% RH), potassium chloride (88% RH) and potassium nitrate (96% RH). 0% RH was achieved by using dehydrated silica gel.

The odour of each pro-fragrance composition was then compared to the corresponding CB[n]-free odour molecule. The released intensity of three pro-fragrance compositions containing high impact odour molecules and CB[n] was investigated using an odour characterization test. A six member trained panel characterized the odour of such compositions under different relative humidity conditions in terms of preference, as a percentage of the panel, and odour intensity using a scale of 1 to 9, with 1 being substantially odourless and 9 being most pungent. The results are reported in Table 1.

Table [1] shows the released intensity of three powerful odour molecules, both complexed with CB[n] and uncomplexed, under different relative humidity conditions and room temperature (20° C.±2).

| | Average odour intensity (Scale 1 to 9) | | | | | Panel chose as preferred (%) | | | | |
|---|---|---|---|---|---|---|---|---|---|---|
| | Relative humidity(%) | | | | | | | | | |
| | 0 | 55 | 75 | 88 | 96 | 0 | 55 | 75 | 88 | 96 |
| Citral | 1.3 | 2.3 | 2.2 | 2.2 | 2.8 | 17 | 0 | 0 | 0 | 0 |
| Citral/CB[n] complex | 2.8 | 5.3 | 7.2 | 8.0 | 7.8 | 83 | 100 | 100 | 100 | 100 |
| Cis-3-hexenyl acetate | 1.4 | 1.4 | 2.8 | 2.2 | 2.2 | 100 | 20 | 60 | 0 | 0 |
| Cis-3-hexenyl acetate/CB[n] complex | 1 | 2.8 | 2.8 | 4.6 | 5.4 | 0 | 80 | 40 | 100 | 100 |
| Ethyl Linalool | 2.4 | 2 | 4.2 | 3.6 | 2 | 100 | 20 | 40 | 20 | 0 |
| Ethyl Linalool/CB[n] complex | 1 | 3.6 | 4.4 | 5.6 | 6.6 | 0 | 80 | 60 | 80 | 100 |

Outcome: it is apparent from the table that in the presence of CB[n], the release of all high impact odour molecules is triggered by humidity. A significant release of Citral is observed at 55% RH, while Cis-3-hexenyl acetate and Ethyl Linalool are significantly released at 88% RH and 75% RH respectively.

Example 2 Moisture-Induced Release of Perfume Accord

A model perfume accord was obtained by mixing 10% by weight of cis-3-Hexenyl acetate, 10% by weight of Citral, 30% by weight of Ethyl linalool, 5% by weight of beta-Ionone, 10% by weight of Hexyl salicylate, 10% by weight of Cyclaprop, 10% by weight of Verdox and 20% by weight of Ethylene brassylate, based on the total weight of the composition. The pro-fragrance compositions were formulated by adding 100 μL (1.25% weight in ethanol/water mixture) of perfume to a glass slide coated with 100 μL (10% weight in water) of the CB[n] composition used in Example 1, or 400 μL (2.5% weight in water) of purified CB[7] (which can be obtained from Sigma-Aldrich) that had been dried prior to the addition of the pro-fragrance composition. After 5 h equilibration in open space and at room temperature, each glass slide was placed in an empty 500 mL flask under different relative humidity conditions for odour evaluation. The six-member panel was asked to choose one pro-fragrance composition in terms of its closeness to the original uncomplexed accord and of its hedonic character. The results are reported in Table 2.

Table [2] shows the advantage of using CB[n] over CB[7] in a pro-fragrance composition containing a mixture of molecule odours (perfume) to provide an improved hedonic release profile at a moderate and high relative humidity and room temperature (20° C.±2).

| | Panel chose as preferred (%) | | |
|---|---|---|---|
| Relative humidity (%) | 0 | 55 | 88 |
| Pro-fragrance Composition (CB[7]) | 50 | 0 | 15 |
| Pro-fragrance Composition (CB[n]) | 50 | 100 | 85 |

Outcome: it is apparent from the table that the advantage of adding CB[n] to a perfume pro-fragrance composition is to provide a pleasant hedonic character profile at moderate (55%) and high (88%) relative humidity. Furthermore, the odour characteristics of the perfume released by the CB[n] composition were found to be much closer to those of the neat, uncomplexed model perfume accord.

Example 3 Malodour-Induced Fragrance Release

The pro-fragrance composition comprising CB[n] and Citral was formulated following the procedure described in previous examples. After 5 h equilibration in open space and at room temperature (20° C.±2), two glass sides containing the pro-fragrance were placed in two different empty 500 mL flasks, an additional glass slide with a fish malodour (Ammonia, triethanolamine and dimethylalmine, each 1.5 weight % in ethanol solution) was placed inside one of the flasks. As a control, a third flask containing a glass slide with the malodour and a glass slide with pro-fragrance that contained no CB was prepared. After 45 min exposure to the malodour in the flasks, a panel of seven trained members was asked to describe the odour character and rate odour intensity of all three flasks and to evaluate the presence and absence of fish malodour. The results are reported in Table 3.

Table [3] shows how a pro-fragrance composition containing CB[n] and Citral is capable of counteracting fish malodour via molecular displacement.

| | Odour Character | Average odour intensity (Scale 1 to 9) |
|---|---|---|
| Malodour/Citral | 100% described as fish | 7.6 |
| Pro-fragrance Citral/CB[n] | 100% described as citrus | 4.8 |
| Pro-fragrance Citral/CB[n] + Fish malodour | 100% described as citrus | 7.7 |

Outcome: it is apparent from the table that citral is released from CB[n] in the presence of fish malodour. This release is most likely due to molecular exchange in the CB[n] cavity. This dual process masks the fish malodour and promotes the controlled release of citral.

Example 4 Malodour-Induced Fragrance Release from CB[n], Compared to CB[7]

A seven member trained panel characterized the odour of pro-fragrance compositions of CB[n] or CB[7] and Citral in the presence and absence of fish malodour. The pro-fragrance composition was formulated following the procedure described in previous examples. After 5 h neutralization time at room temperature (20° C.±2), two glass sides containing the pro-fragrance (one with CB[n] and the other with CB[7]) were placed in two different empty 500 mL flasks, another two identical flasks were prepared containing the malodours. After 45 min of the malodours being in the flasks, the panel was asked to describe the odour character and rate odour intensity of all four flasks.

Table [4] shows the advantage of using CB[n] over CB[7] in a pro-fragrance composition containing citral for counteracting fish malodour via molecular displacement.

| | Odour Character | Average odour intensity (Scale 1 to 9) |
|---|---|---|
| Pro-fragrance Citral/CB[n] | 100% described as Citrus | 5.3 |
| Pro-fragrance Citral/CB[n] + Fish malodour | 71% described as citrus | 7.7 |
| Pro-fragrance Citral/CB[7] | 100% described as citrus | 3.0 |
| Pro-fragrance Citral/CB[7] + Fish malodour | 86% described as a mix of fish and citrus | 8.1 |

Outcome: it is apparent from the table that using a pro-fragrance composition comprising CB[n] and perfume is advantageous for counteracting fish malodour over CB[7].

Example 5 Malodour-Induced Perfume Accord Release from CB[n]

A seven member trained panel characterized the odour of a pro-fragrance composition of CB[n] and model perfume accord in the presence and absence of fish malodour (Ammonia, triethanolamine and dimethylalmine, each 1.5 weight % in ethanol solution). The pro-fragrance composition was formulated following the procedure described in example 2. After 5 h neutralization time at room temperature (20° C.±2), two glass slides containing the pro-fragrance were placed in two different empty 500 mL flasks, an additional glass slide with the malodour was placed inside one of the flasks. As a control, a third flask containing only a glass slide with the malodour was prepared. After 45 min of the malodours being in the flasks, the panel was asked to describe the odour character and rate odour intensity of all three flasks. The results are reported in Table 5.

Table [5] shows how a pro-fragrance composition containing CB[n] and a mixture of odour molecules (perfume) is capable of counteracting fish malodour via molecular displacement.

| | Odour Character | Average odour intensity (Scale 1 to 9) |
|---|---|---|
| Fish malodour/Perfume | 100% described as fish | 8.0 |
| Pro-fragrance perfume/CB[n] | 100% described as citrus/Floral | 3.1 |
| Pro-fragrance perfume/CB[n] + Fish malodour | 100% described as citrus | 6.9 |

Outcome: it is apparent from the table that the model perfume accord is released from CB[n] in the presence of fish malodour. This is most likely due to molecular exchange in the CB[n] cavity. The pleasant hedonic release of the perfume accord in the presence of CB[n] helps mask the fish malodour.

The invention claimed is:

1. A pro-fragrance composition comprising a plurality of complexes of cucurbiturils with one or more fragrance molecule(s), wherein the cucurbiturils are present as a mixture, wherein the mixture comprises 0.1-20% by weight of CB[5], 35-75% by weight of CB[6], 10-45% by weight of CB[7] and 10-30% by weight of CB[8], based on a total weight of cucurbiturils in the composition, and wherein the complexed fragrance molecule(s) is released when the composition is exposed to a stimulus.

2. The composition according to claim 1, wherein the composition further comprises CB[n], wherein n is an integer of 4 or 9-20.

3. The composition according to claim 1, wherein the mixture comprises 1-20% by weight of CB[5], based on the total weight of cucurbiturils in the composition.

4. The composition according to claim 1, wherein the mixture comprises 35-60% by weight of CB[6], based on the total weight of cucurbiturils in the composition.

5. The composition according to claim 1, wherein the mixture comprises 20-45% by weight of CB[7], based on the total weight of cucurbiturils in the composition.

6. The composition according to claim 1, wherein the mixture comprises 22-27% by weight of CB[7], based on the total weight of cucurbiturils in the composition.

7. The composition according to claim 1, comprising more than one fragrance, wherein the more than one fragrance forms a perfume accord or a full perfume, and wherein said perfume accord or full perfume is released when the composition is exposed to a stimulus.

8. The composition according to claim 7, wherein the perfume accord or the full perfume has an odour character which is substantially unchanged when the perfume accord or the full perfume is released.

9. The composition according to claim 1, wherein the stimulus is an increase of moisture in the composition or an addition of liquid water to the composition.

10. The composition according to claim 1, wherein the stimulus is a change in the ionic strength or pH of the composition.

11. The composition according to claim 1, wherein the stimulus is the application of heat to the composition.

12. The composition according to claim 1, wherein the stimulus is the addition of another molecule, whereby the fragrance is released via molecular exchange.

13. The composition according to claim 12, wherein the another molecule is a nitrogen-containing molecule, a sulphur-containing molecule or an oxygen-containing molecule.

14. A product comprising the composition as defined in claim 1.

15. The product according to claim 14, wherein the product is for laundry care, home care or personal care.

16. The product according to claim 15, wherein the laundry care, home care or personal care product is in the form of a powder, granulates, a tablet or single-dose units, dispersion, emulsion, micro-emulsion or solution, a hydro-alcoholic product, wipe or sponge, aerosol or liquid dispenser, cream, balsam, polish or wax.

17. A method for the preparation of pro-fragrance complexes of cucurbiturils and fragrance molecules, wherein the cucurbiturils are a mixture comprising 0.1-20% by weight of CB[5], 35-75% by weight of CB[6], 10-45% by weight of CB[7] and 10-30% by weight of CB[8], based on a total weight of cucurbiturils in the composition, the method comprising the step of mixing a fragrance solution with the cucurbiturils, thereby to form complexes of the cucurbiturils with the fragrance.

18. A method of counteracting malodour comprising application of the composition as defined in claim 1.

* * * * *